US012171887B2

(12) United States Patent
Andries et al.

(10) Patent No.: US 12,171,887 B2
(45) Date of Patent: Dec. 24, 2024

(54) LONG-ACTING FORMULATIONS

(71) Applicant: Janssen Pharmaceutica NV, Beerse (BE)

(72) Inventors: Koenraad Jozef Lodewijk Marcel Andries, Beerse (BE); Maristella Bernini, Beerse (BE); Esther Dina Guido Basstanie, Zandhoven (BE)

(73) Assignee: Janssen Pharmaceutica NA, Beerse (BE)

( * ) Notice: Subject to any disclaimer, the term of this patent is extended or adjusted under 35 U.S.C. 154(b) by 0 days.

(21) Appl. No.: 17/469,021

(22) Filed: Sep. 8, 2021

(65) Prior Publication Data

US 2022/0047522 A1 Feb. 17, 2022

Related U.S. Application Data

(63) Continuation of application No. 16/630,676, filed as application No. PCT/EP2018/069066 on Jul. 13, 2018, now Pat. No. 11,141,384.

(30) Foreign Application Priority Data

Jul. 14, 2017 (EP) .................................... 17181354
Apr. 16, 2018 (EP) .................................... 18167463

(51) Int. Cl.
| | |
|---|---|
| *A61K 9/51* | (2006.01) |
| *A61K 9/00* | (2006.01) |
| *A61K 9/10* | (2006.01) |
| *A61K 31/47* | (2006.01) |
| *B82Y 5/00* | (2011.01) |

(52) U.S. Cl.
CPC .......... *A61K 9/5192* (2013.01); *A61K 9/0019* (2013.01); *A61K 9/10* (2013.01); *A61K 31/47* (2013.01); *B82Y 5/00* (2013.01)

(58) Field of Classification Search
CPC ...... A61K 9/5192; A61K 9/0019; A61K 9/10; A61K 31/47; B82Y 5/00
See application file for complete search history.

(56) References Cited

U.S. PATENT DOCUMENTS

| | | | |
|---|---|---|---|
| 5,346,702 | A | 9/1994 | Na et al. |
| 5,352,459 | A | 10/1994 | Hollister et al. |
| 8,546,428 | B2 | 10/2013 | Hegyi et al. |
| 2011/0268803 | A1 | 11/2011 | Prud'Homme et al. |
| 2017/0027933 | A1 | 2/2017 | Mundhra et al. |

FOREIGN PATENT DOCUMENTS

| | | | |
|---|---|---|---|
| WO | WO 01/87266 | 11/2001 | |
| WO | WO 2004/011436 | 2/2004 | |
| WO | WO 2006/067048 | 6/2006 | |
| WO | WO 2006/125769 | 11/2006 | |
| WO | WO 2007/147882 | 12/2007 | |
| WO | WO-2007147882 A2 * | 12/2007 | ............. A61K 31/00 |
| WO | WO 2010/065730 | 6/2010 | |
| WO | WO 2012/140220 | 10/2012 | |
| WO | WO 2016/022853 | 2/2016 | |
| WO | WO 2016/120258 | 8/2016 | |
| WO | WO 2016/179231 | 11/2016 | |
| WO | WO-2016179231 A1 * | 11/2016 | ........... A61K 31/428 |
| WO | WO 2017/066053 | 4/2017 | |
| WO | WO 2018/226512 | 12/2018 | |
| WO | WO 2019/012100 | 1/2019 | |
| WO | WO 2022/008643 | 1/2022 | |
| WO | WO 2022/008644 | 1/2022 | |
| WO | WO 2022/008645 | 1/2022 | |

OTHER PUBLICATIONS

Gelber Robert et al, "The Diarylquinolone R207910 is Bactericidal against *Mycobacterium leprae* in mice and at Low Dose Administered Intermittently", Antimicrobial agents and Chemotherapy, Sep. 2009, vol. 53, No. 9, pp. 3989-3991.
Jary et al., "Bedaquiline loaded lipid nanoparticles: formulation, optimisation and in vitro assays", May 1, 2016.
Ji et al, "Bacterial Activities of R207910 and other Antimicrobial Agents against *Mycobacterium leprae* in Mice", Antimicrobial agents and Chemotherapy, vol. 50 No 4, pp. 1558-1560. 2006.
Lanoix, J.P. et al, Novel regimens identified in mice for treatment of latent tuberculosis infection in contacts of multidrug-resistant tuberculosis cases., Antimicrob. Agents Chemother., vol. 58, pp. 2316-2321, 2014.
Lessem et al., An Activist's Guide to Bedaquiline (Sirturo), pp. 1-8, 2013.
Nasiruddin et al: "Nanotechnology-Based Approach in Tubercolosis Treatment", Tuberculosis Research and Treatment, vol. 2017, pp. 1-12.
Singh et al: "Advances in nanotechnology-based carrier systems for targeted delivery of bioactive drug molecules with special emphasis on immunotheraphy in drug resistant tuberculosis—a critical review", Drug Delivery., vol. 23, No. 5, pp. 1676-1698, 2016.
Zhang, T. et al, Short-course chemotherapy with TMC207 and rifapentine in a murine model of latent tuberculosis infection. Am. J Respir. Crit. Care Med., vol. 184, pp. 732-737, 2011.
Zhang, T. et al, Short-course therapy with daily rifapentine in a murine model of latent tuberculosis infection. Am.J Respir Crit Care Med., vol. 180, pp. 1151-1157, 2009.
Ahire et al, Parenteral Nanosuspensions: a brief review from solubility enhancement to more novel and specific applications, Acta Pharmaceuticals, vol. 8, issue 5, p. 733-755, 2018.
Baert L, et al, . Development of a long-acting injectable formulation with nanoparticles of rilpivirine (TMC278) for HIV treatment. Eur J Pharm Biopharm. 72 (2009), pp. 502-508.

(Continued)

*Primary Examiner* — Robert S Cabral
(74) *Attorney, Agent, or Firm* — Sofia Kopelevich

(57) ABSTRACT

This invention concerns pharmaceutical compositions for administration via intramuscular or subcutaneous injection, comprising micro- or nanoparticles of the anti-TB compound bedaquiline, suspended in an aqueous pharmaceutically acceptable carrier, and the use of such pharmaceutical compositions in the treatment and prophylaxis of a pathogenic mycobacterial infection.

19 Claims, 7 Drawing Sheets

(56) References Cited

OTHER PUBLICATIONS

Figure 1:
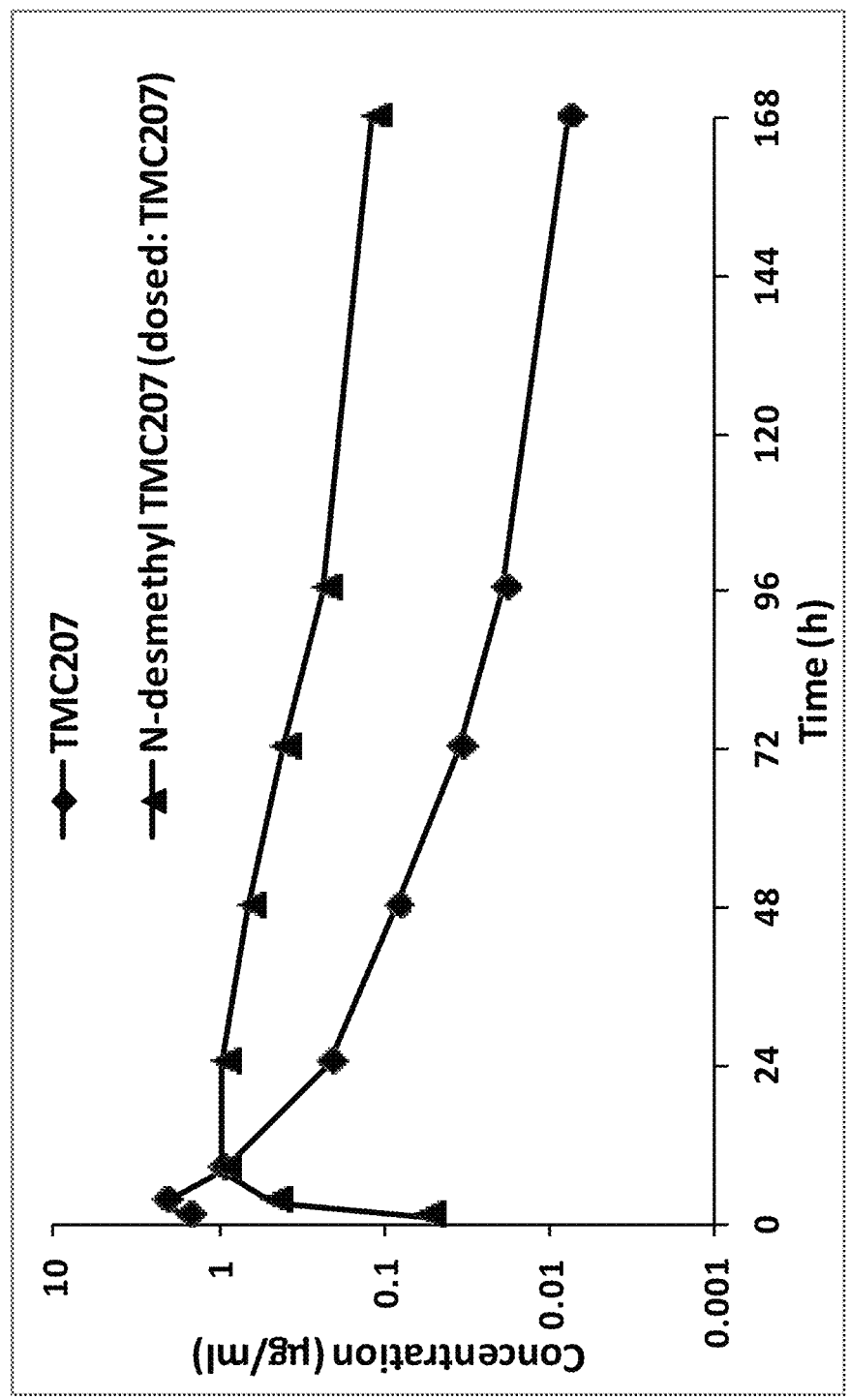

D'Souza A and Shegokar R, 'Polyethylene glycol (PEG): a versatile polymer for pharmaceutical applications', Expert opinion on Drug delivery, vol. 13, issue 9, p. 1257-1275, 2016.
De Matteis et al, "New active formulations against M. tuberculosis: Bedaquiline encapsulation in lipid nanoparticles and chitosan nanocapsules", Chemical Engineering Journal, Elsevier, Amsterdam, NL, vol. 340,Dec. 22, 2017, pp. 181-191.
Dutz et al, Nanomaterials, vol. 7(12), 2017, pp. 453.
Gomez et al., Materials Research Bulletin, vol. 48(10), 2013, 4051-4057.
Guo C et al, Optimizing of Extended-Release ZL-004 Nanosuspensions for in vivo Pharmacokinetic study to Enchase Low soubility and Compliance; Molecules, vol. 24, issue 7, p. 1-12, Dec. 20, 2018.
Kaushik A et al: Activity of a long-acting injectable Bedaquiline Formulation in a paucibacillay Mouse model of latent Tubercolosis infection, Antimicrobial Agents and Chemotherapy, Mar. 2019, vol. 63, issue 4, p. 1-10.
Owen A. et al., "Strengths, weaknesses, opportunities and challenges for long acting injectable therapies: Insights for applications in HIV therapy", Adv Drug Deliv Reviews 103 (2016) pp. 144-156.
Suñol JJ et al: "Thermal Analysis of a Polyethylene Glycol (PEG 4000): T-CR-T Diagram Construction", Journal of Thermal Analysis and Calorimetry, Kluwer Academic Publishers, Dordrecht, NL, vol. 61, No. 3, 2000, pp. 711-718.
Della Porta P. et al., "Production and characterization of mPEGPLGA nanoparticles for Bedaquiline release to fight the multi drug resistance", 2016, https://www.gruppotpp.it/wp-content/uploads/2016/12/Tesi-Piera-Della-Porta-LM_ex.pdf.
International Search Report PCT/EP2021/068956 dated Sep. 23, 2021.
International Search Report PCT/EP2021/068957 dated Sep. 21, 2021.
International Search Report PCT/EP2021/068958 dated Sep. 21, 2021.
Remenar Julius F., Making the Leap from Daily Oral Dosing to Long-Acting Injectables: Lessons from the Antipsychotics, Mol. Pharmaceutics, vol. 11, No. 6, pp. 1739-1749 (2014).
Rajoli et al., "Simulation of long-acting administration of antituberculosis agents using pharmacokinetic modelling", 9th International Workshop on Clinical Pharmacology of Tuberculosis Drugs, Liverpool, UK, Oct. 24, 2016, Abst# O_13.
Swindells et al., "Long-acting formulations for the treatment of latent tuberculous infection: opportunities and challenges" Int J Tuberc Lung Dis, 22(2):125-132, 2018.
International Search Report and Written PCT/EP2018/069066 dated Oct. 4, 2018.

\* cited by examiner

LONG-ACTING FORMULATIONS

CROSS REFERENCE TO RELATED APPLICATIONS

This application is a continuation of U.S. application Ser. No. 16/630,676, filed Jan. 13, 2020, which is the national stage of PCT Application No. PCT/EP2018/069066, filed Jul. 13, 2018, which claims priority from European Patent Application No. 17181354.6 filed Jul. 14, 2017 and European Patent Application No. 18167463.1 filed April 16. 2018, the entire disclosures of which are hereby incorporated by reference in their entirety.

FIELD OF THE INVENTION

This invention concerns pharmaceutical compositions for administration via intramuscular or subcutaneous injection, comprising micro- or nanoparticles of the ATP synthase inhibitor compound, bedaquiline (marketed as Sirturo®, where bedaquiline is in the form of its fumarate salt), suspended in an aqueous pharmaceutically acceptable carrier, and the use of such pharmaceutical compositions in the treatment of bacterial infections, e.g. tuberculosis and the like.

BACKGROUND OF THE INVENTION

Bedaquiline is a known anti-tuberculosis drug used in various combinations. It may be formulated in the form of a pharmaceutically acceptable salt, such as in the form of bedaquiline fumarate, marketed as Sirturo®. It is thought to act as an ATP synthase inhibitor, possessing a selectivity index of more than 20000 for mycobacterial ATP synthase versus eukaryotic mitochondrial ATP synthase.

Bedaquiline has already been reported as being useful in the treatment of mycobacterial infections, as well as being useful in killing dormant, latent, persistent mycobacteria, in particular *Mycobacterium tuberculosis*, and can consequently be used to treat latent TB.

Such use of bedaquiline has been described in several publications including international patent documents WO 2004/011436 and WO 2006/067048. It is also known that bedaquiline is bactericidal against *mycobacterium leprae*, for example as described in "Bacterial Activities of R207910 and other Antimicrobial Agents against *Mycobacterium leprae* in Mice", Antimicrobial agents and Chemotherapy, April 2006, p 1558, and "The Diarylquinolone R207910 is Bactericidal against *Mycobacterium leprae* in mice and at Low Dose Administered Intermittently", Antimicrobial agents and Chemotherapy, September 2009, p 3989.

The goal of long-acting formulations can be to reduce drug burden. This is particularly useful for treatment regimens that may last several months.

The number and/or volume of dosage forms that need to be administered are commonly referred to as "pill burden". A high pill burden is undesirable for many reasons, such as the frequency of intake, often combined with the inconvenience of having to swallow large dosage forms, as well as the need to store and transport a large number or volume of pills. A high pill burden increases the risk of patients not taking their entire dose, thereby failing to comply with the prescribed dosage regimen. As well as reducing the effectiveness of the treatment, this may also lead to the emergence of resistance (e.g. in the case of bedaquiline, bacterial resistance).

It would be attractive to provide therapy involving the administration of dosage forms at long time intervals such as one week or longer, or even one month or longer.

Various formulations are known in the art, including long-acting ones. For instance, micro- and nano-suspension technology is known for achieving long-acting formulations in the field of anti-HIV drugs, for instance as described in international patent applications WO 2007/147882 and WO 2012/140220. Further, nanoparticles known in the prior art have been described, for example, in EP-A-0 499 299. Such particles have an average particle size in the submicron range and consist of particles of a crystalline drug substance having a surface modifier adsorbed on their surface. Nanoparticles have also been used to formulate poorly water-soluble active ingredients.

Long-acting formulations of the anti-tuberculosis drug bedaquiline are now described. It now has been found that the compound bedaquiline can be formulated into micro- or nanoparticles and that such formulations can be used as long-acting (or depot) formulations, which may find use in the treatment of various bacterial infections, including e.g. tuberculosis.

Challenges for such formulations would have been thought to exist based on pharmacokinetic (PK) properties of tuberculosis drugs, including bedaquiline, and the need to keep plasma levels above a minimum level bearing those PK properties in mind. The mean terminal elimination half-life of bedaquiline and the N-monodesmethyl metabolite (also known as the M2 metabolite) is approximately 5.5 months. This long terminal elimination phase likely reflects slow release of bedaquiline and M2 from peripheral tissues. In October 2016 at the UNION conference in Liverpool Susan Swindells from the University of Nebraska Medical Center presented on "Experience from Long-Acting HIV Drug Development" where it was summarsied that existing tuberculosis drugs were not ideal candidates (for long-acting) and reliable pharmacodynamic models were lacking.

The invention furthermore relates to the intermittent administration of these micro- or nanoparticle formulations at time intervals of one week or longer that result in plasma levels that may be sufficient to suppress the growth of the mycobacterial infection. This allows for a reduced number of administrations thereby being beneficial in terms of pill burden and drug compliance of the patient. The micro- or nanoparticle formulations of bedaquiline of the invention therefore may be useful in the long-term treatment of mycobacterial infections (e.g. tuberculosis, including latent tuberculosis, and leprosy).

The intermittent administration of micro- or nanoparticle formulations of bedaquiline at time intervals of one week or longer furthermore results in plasma levels that may be sufficient to provide prevention against transmission of mycobacterial infection. Also in this instance, a reduced number of administrations is required, which again is advantageous in terms of pill burden and drug compliance of the individual at risk of being infected.

SUMMARY OF THE INVENTION

The present invention is concerned with a pharmaceutical composition for administration by intramuscular or subcutaneous injection, comprising a therapeutically effective amount of bedaquiline, or a pharmaceutically acceptable salt thereof, in the form of a suspension of micro- or nanoparticles comprising:

(a) bedaquiline, or a pharmaceutically acceptable salt thereof, in micro- or nanoparticle form, and a surface modifier; and
(b) a pharmaceutically acceptable aqueous carrier, wherein such a composition may be referred to herein as "composition(s) of the invention".

The composition of the invention is a suspension, by which we mean that the bedaquiline active ingredient is suspended in the pharmaceutically acceptable aqueous carrier.

The composition of the invention (i.e. the suspension) contains a surface modifier, which may be adsorbed onto the surface of the active ingredient bedaquiline.

In an embodiment, the present invention may therefore concern a pharmaceutical composition for administration by intramuscular or subcutaneous injection, comprising a therapeutically effective amount of bedaquiline, or a pharmaceutically acceptable salt thereof, in the form of a suspension of micro- or nanoparticles comprising:
(a) bedaquiline, or a pharmaceutically acceptable salt thereof, in micro- or nanoparticle form, having a surface modifier adsorbed to the surface thereof; and
(b) a pharmaceutically acceptable aqueous carrier; wherein the bedaquiline active ingredient is suspended.

The invention further concerns a method of treating a subject infected with pathogenic mycobacteria such as *Mycobacterium tuberculosis, M. bovis, M. leprae, M. avium* and *M. marinum*. In an embodiment, the mycobacteria is *Mycobacterium tuberculosis* (including the latent or dormant form) or *Mycobacterium leprae*. The compositions of the invention may be particularly suitable for the treatment of *Mycobacterium leprae* and the latent or dormant form of *Mycobacterium tuberculosis*. This is because for treating these specific infections, a lower concentration of bedaquiline in the plasma may be effective against such infection, for instance as described in Antimicrobial Agents and Chemotherapy, September 2009, p. 3989-3991 by Robert Gelber, Koen Andries et al (the contents of which are hereby incorporated by reference, and wherein, essentially, it is reported that low and intermittent dosing with bedaquiline holds promise for leprosy patients; whereas minimal dose killing 99% of bacilli for *M. tuberculosis* is 30 mg/kg/wk, for *M. lepra* it is <5.0 mg/kg/wk, and hence dosing once a month may be as efficient as 5 days a week; other publications of the effect of bedaquiline on *Mycobacterium leprae* in mice include Antimicrobial Agents and Chemotherapy, April 2006, p. 1558-1560 by Baohong Ji, Koen Andries et al—the contents of which are also hereby incorporated by reference). Hence, the compositions of the invention may be particularly suitable in a method of treating a subject infected with *Mycobacterium leprae* or the latent/dormant form of *Mycobacterium tuberculosis*. Such methods of treating a subject infected with pathogenic mycobacteria comprise the administration, by intramuscular or subcutaneous injection, of a therapeutically effective amount of a pharmaceutical composition as specified above or hereinafter. Or, alternatively, the invention concerns the use of a pharmaceutical composition as specified above or hereinafter, for the manufacture of a medicament for treating pathogenic mycobacteria infection (or for using such medicament in a particular treatment regime as described herein). In one embodiment, the composition is for the long-term treatment of pathogenic mycobacteria infection. In an embodiment, the pathogenic mycobacterial infection may such as described above or hereinafter, such as an infection that requires long-term treatment (in a further embodiment, an infection that further may be treated at relatively low plasma concentration levels of bedaquiline or its active metabolite, for instance latent/dormant *Mycobacterium tuberculosis* or, in a particular embodiment, *Mycobacterium leprae*).

In another aspect, there is provided a method for the long term treatment of a subject infected with pathogenic mycobacteria such as *Mycobacterium tuberculosis, M. bovis, M. leprae, M. avium* and *M. marinum*, said method comprising the administration of an effective amount of a pharmaceutical composition as specified above or hereinafter, for administration by intramuscular or subcutaneous injection; wherein the composition is administered or is to be administered intermittently at a time interval that is in the range of one week to one year, or one week to two years. Or, alternatively, the invention concerns the use of a pharmaceutical composition as specified above or hereinafter, for the manufacture of a medicament for the long term treatment of a subject infected with pathogenic mycobacteria such as *Mycobacterium tuberculosis, M. bovis, M. leprae, M. avium* and *M. marinum*, for administration by intramuscular or subcutaneous injection, wherein the composition is administered or is to be administered intermittently at a time interval that is in the range of one week to one year, or one week to two years. Hence, it will be understood that the term "long term treatment" refers to treatment where one dose or one administration (e.g. by intramuscular or subcutaneous injection) will have a persistent therapeutic effect over a time period, as described herein, for instance a persistent therapeutic effect over several hours, weeks or months (e.g. in an embodiment, over a period of at least or up to one month, three months or six months); see examples. Put another way, long term treatment may refer to, where there is more than one dose/administration, the long period of time (as described herein) between the doses/administrations, i.e. the intervals are a long period of time as described herein.

In another aspect, there is provided a method for the long term treatment of a subject infected with pathogenic mycobacteria (e.g. of any of the types as described here), as described herein (e.g. above) wherein one dose or administration (e.g. of the amount described herein, e.g. hereinafter) is provided/required (and has a persistent effect, e.g. over a time period described herein). In another aspect, there is provided such a long term treatment regime, where two such doses or administrations are provided/required, which doses/administrations are given at intervals, wherein the interval time period is that as described herein, e.g. a period of at least or up to one month, three months or six months—for instance for a period of time in which persistent therapeutic effect lasts). In a further embodiment, there is provided such a long term treatment regime, in which three such doses or administrations are provided/required at such intervals as herein described. In yet a further embodiment, there is provided a long term treatment regime as herein described but which is preceded with a lead-in treatment phase (that is not a long term treatment regime, e.g. a once-daily administration course, lasting for one week, two weeks, three weeks or one month).

The invention further concerns a method for the prevention of a pathogenic mycobacterial infection in a subject at risk of being infected by a pathogenic mycobacterial infection, said method comprising administering an amount, effective in preventing a pathogenic mycobacterial infection, of a pharmaceutical composition as specified above or as further specified hereinafter, to said subject. Or alternatively, the invention concerns the use of a pharmaceutical composition as specified above or as further specified hereinafter for the manufacture of a medicament for the prevention of a pathogenic mycobacterial infection in a subject at risk of being infected by a pathogenic mycobacterial infection.

In another aspect the invention relates to a method for the long term prevention of a pathogenic mycobacterial infection in a subject at risk of being infected by a pathogenic mycobacterial infection, said method comprising administering to said subject an effective amount of a pharmaceutical composition as specified above or as further specified hereinafter, wherein the composition is administered or is to be administered intermittently at a time interval that is in the range of one week to one year, or one week to two years.

The present invention furthermore relates to the use of a pharmaceutical composition as specified above or as further specified hereinafter, for the manufacture of a medicament for the long term prevention for the long term prevention of a pathogenic mycobacterial infection in a subject at risk of being infected by a pathogenic mycobacterial infection, wherein the composition is administered or is to be administered intermittently at a time interval that is in the range of one week to one year or one week to two years.

In one embodiment the invention concerns a use or a method as specified herein, wherein the pharmaceutical composition is administered or is to be administered at a time interval that is in the range of one week to one month, or in the range of one month to three months, or in the range of three months to six months, or in the range of six months to twelve months, or in the range of 12 months to 24 months.

In another embodiment the invention concerns a use or a method as specified herein, wherein the pharmaceutical composition is administered or is to be administered once every two weeks, or once every month, or once every three months.

Further pharmaceutical compositions, methods of treatment or prevention, as well as uses for the manufacture of medicaments based on these compositions will be described hereinafter and are meant to be part of the present invention.

The invention is also described with reference to the following figures:

FIG. 1: "Plasma kinetics of TMC207 (bedaquiline; BDQ) and M2 (bedaquiline's metabolite; see herein) in mouse, after a single dose of 30 mg/kg"

Figure 2:
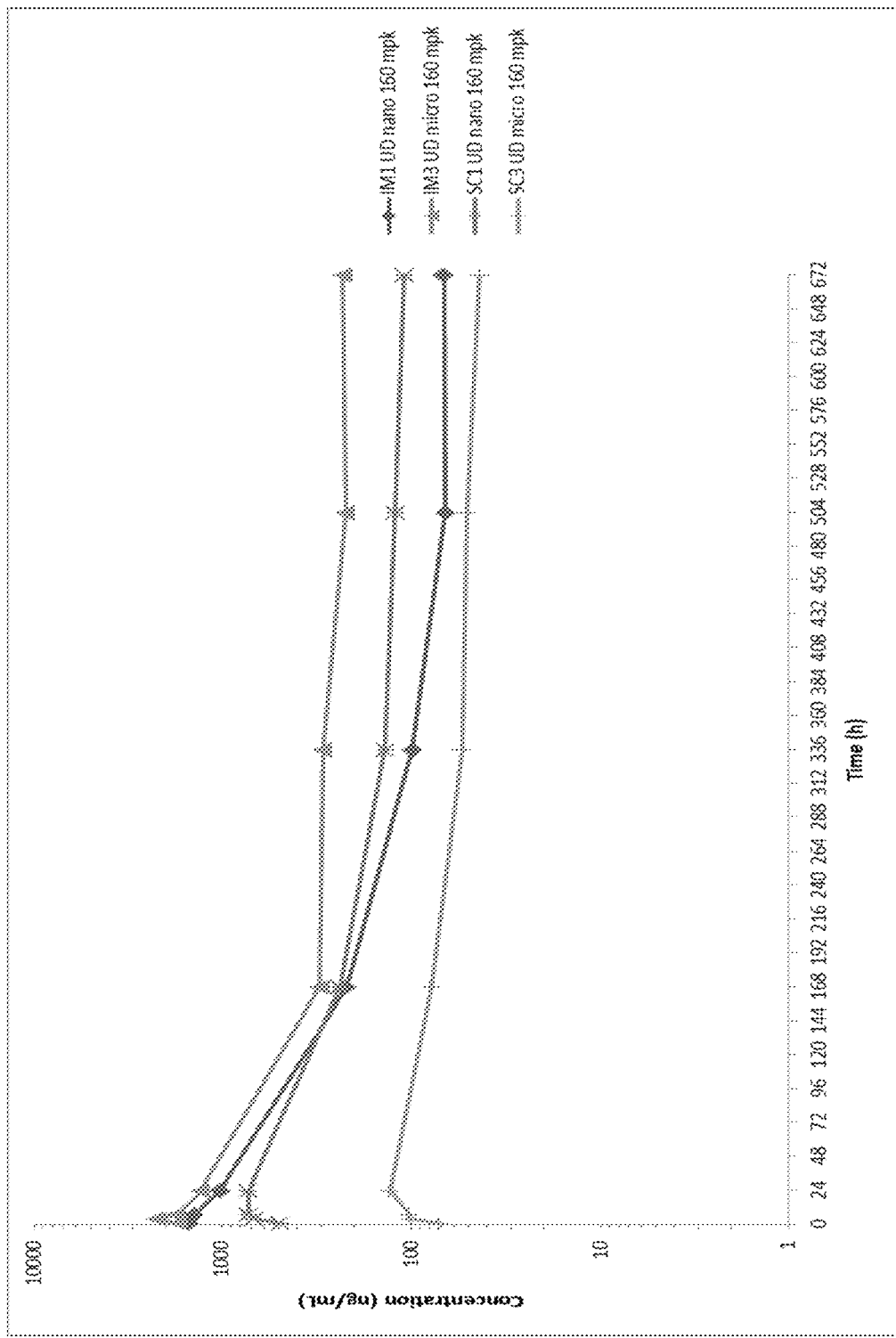

FIG. 2: "Plasma kinetics of TMC207 in mouse when administered IM or SC with 200 mg/ml formulations (specifically formulations of Examples 1A and 1B, i.e. the nano- and micro-suspension, respectively) at a dose of 160 mg/kg" (TMC207 is referred to the in the Figure as "UD")

Figure 3:
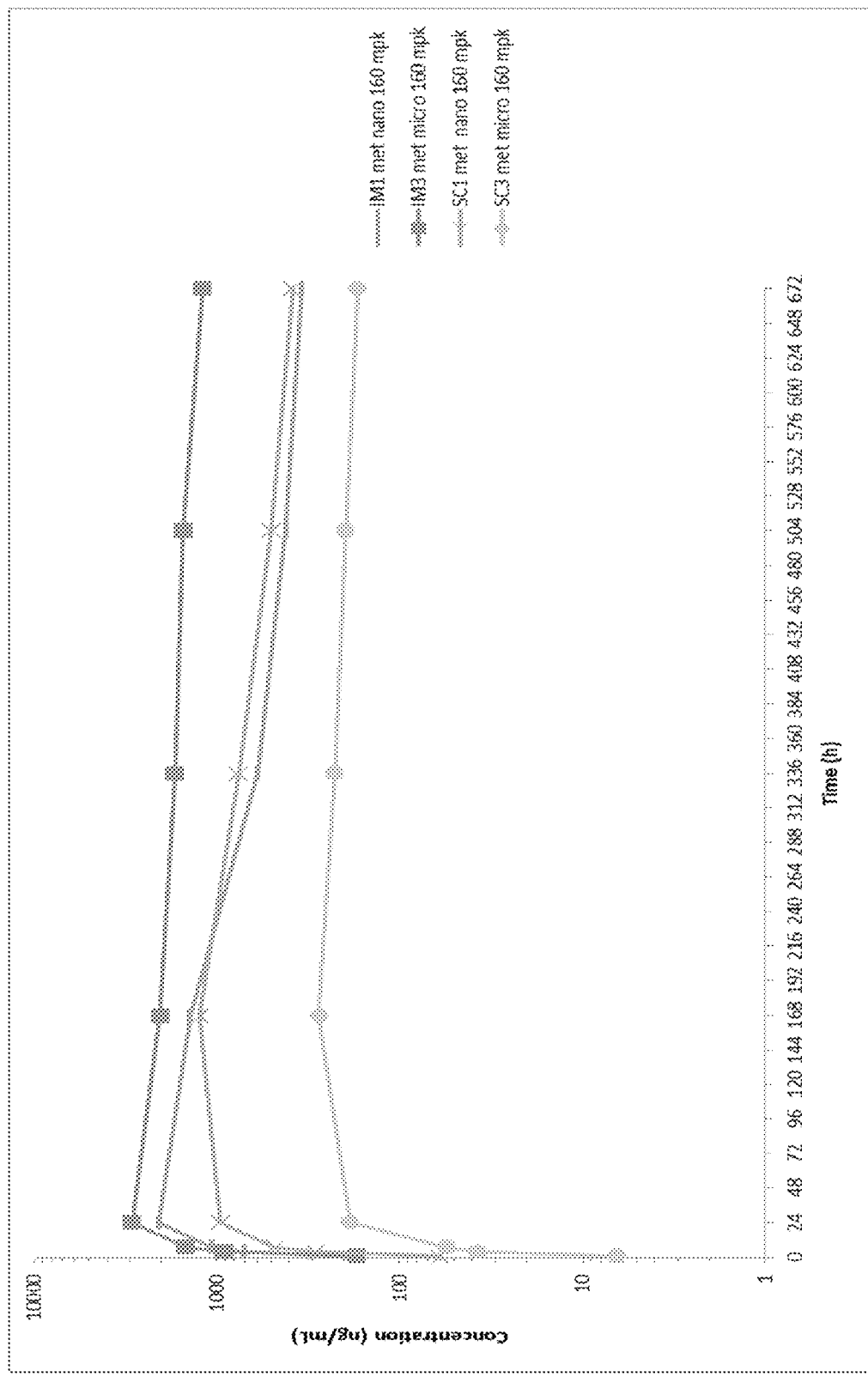

FIG. 3: "Plasma kinetics of M2 in mouse when administered IM or SC with 200 mg/ml formulations (specifically formulations of Examples 1A and 1B, i.e. the nano- and micro-suspension, respectively) at a dose of 160 mg/kg" (M2 is referred to in the Figure as "met")

Figure 4:
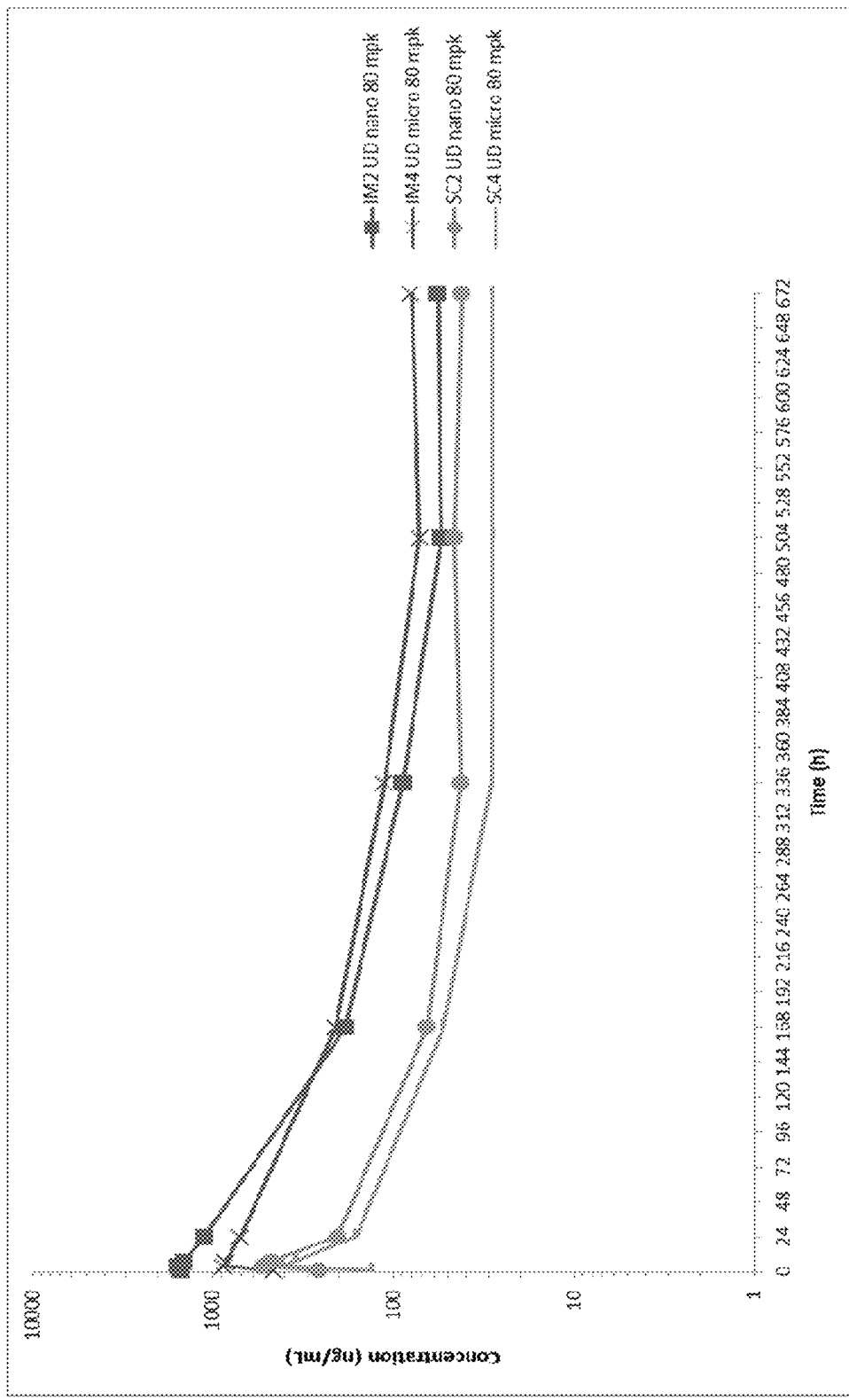

FIG. 4: "Plasma kinetics of TMC207 in mouse when administered IM or SC with 100 mg/ml formulations (specifically formulations of Examples 1C and 1D, i.e. the nano- and micro-suspension, respectively) at a dose of 80 mg/kg" (TMC207 is referred to the in the Figure as "UD")

Figure 5:
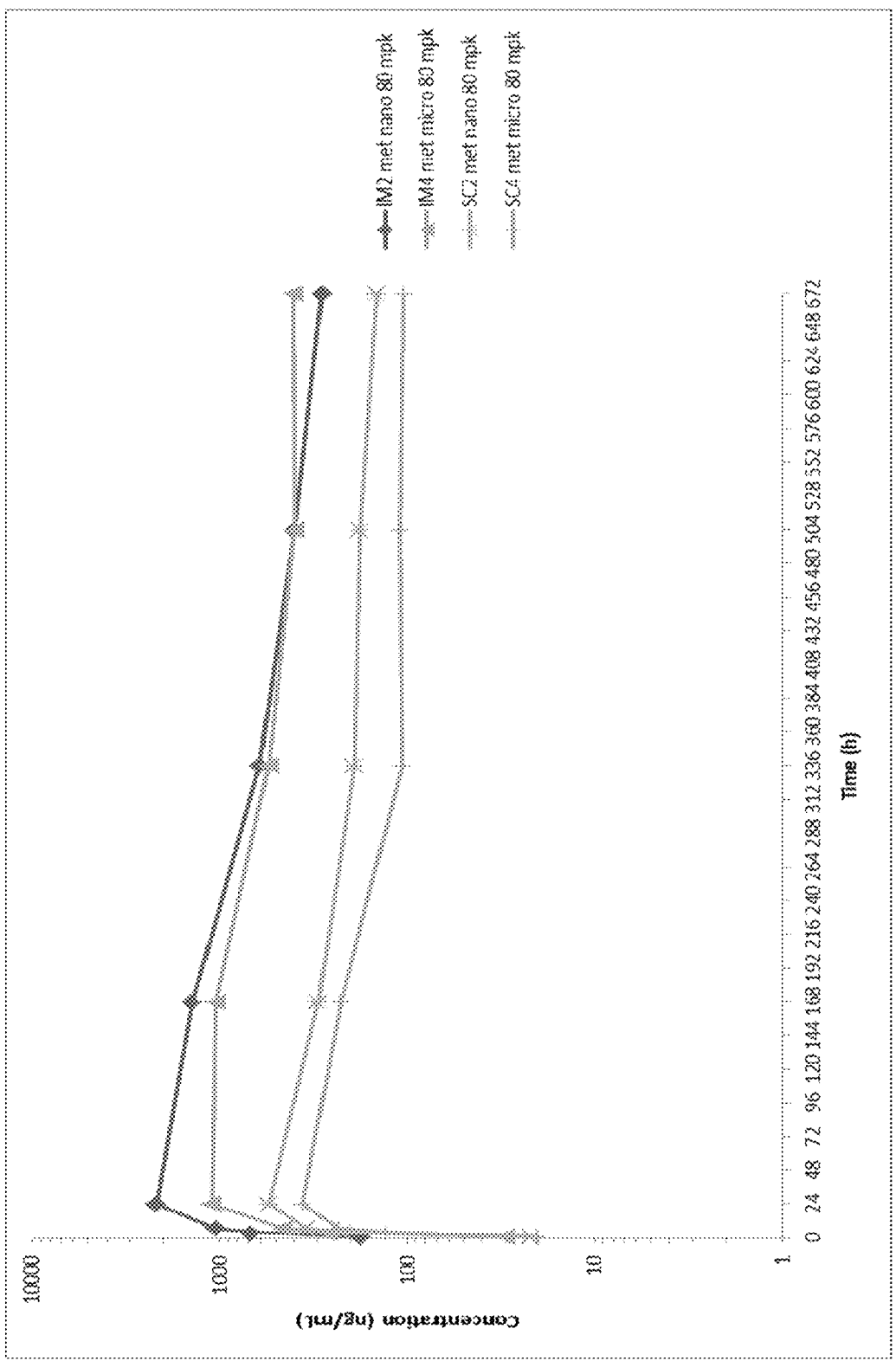

FIG. 5: "Plasma kinetics of M2 in mouse when administered IM or SC with 100 mg/ml formulations (specifically formulations of Examples 1C and 1D, i.e. the nano- and micro-suspension, respectively) at a dose of 80 mg/kg" (M2 is referred to in the Figure as "met")

Figure 6:
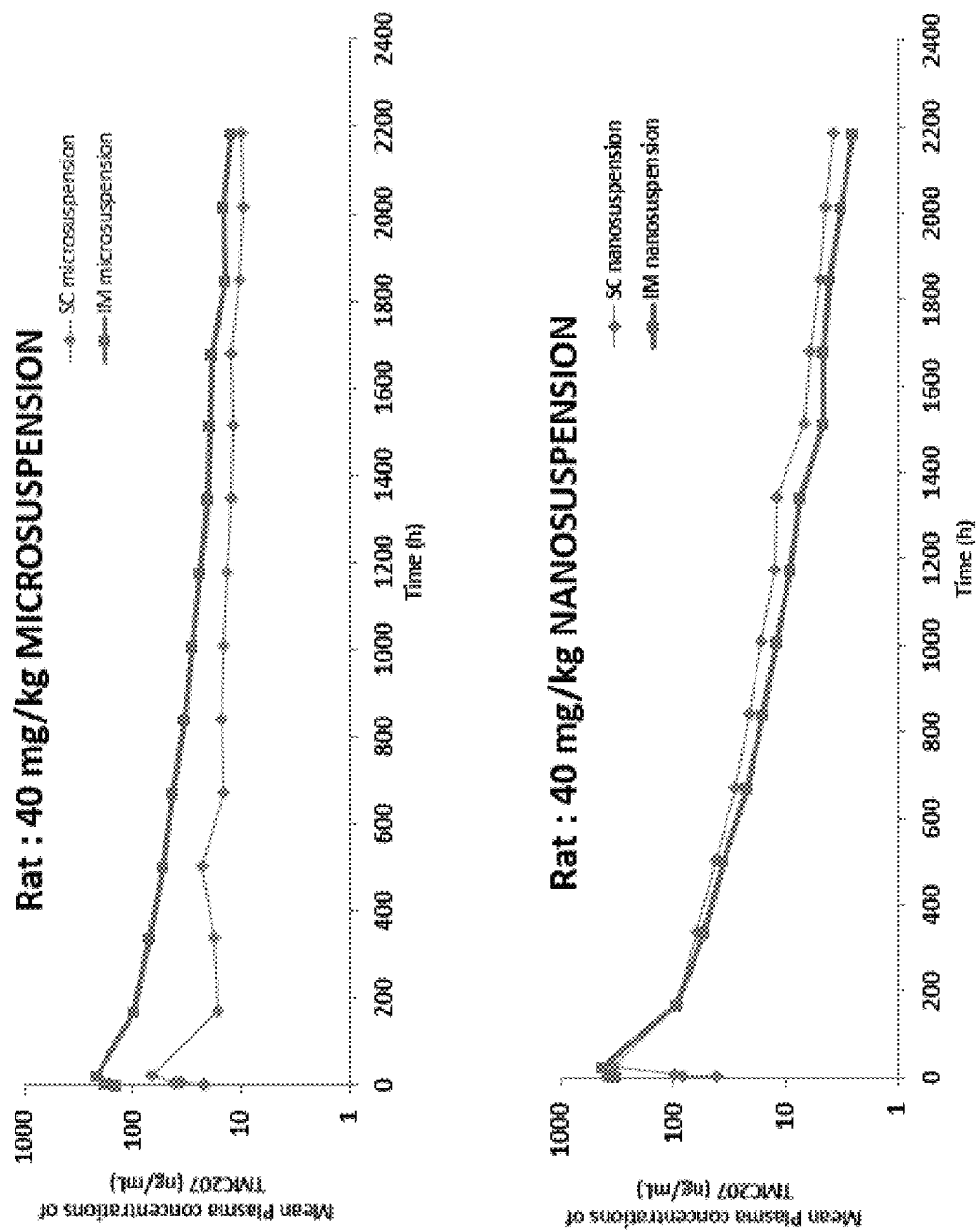

FIG. 6: "Plasma kinetics of TMC207 in male rats when administered IM or SC with 200 mg/ml micro-formulation (see Example 1, Formulation 1B i.e. the micro-suspension) at a dose of 40 mg/kg" and "Plasma kinetics of TMC207 in male rats when administered IM or SC with 200 mg/ml nano-formulation (see Example 1, Formulation 1A, i.e. the nano-suspension) at a dose of 40 mg/kg"

Figure 7:
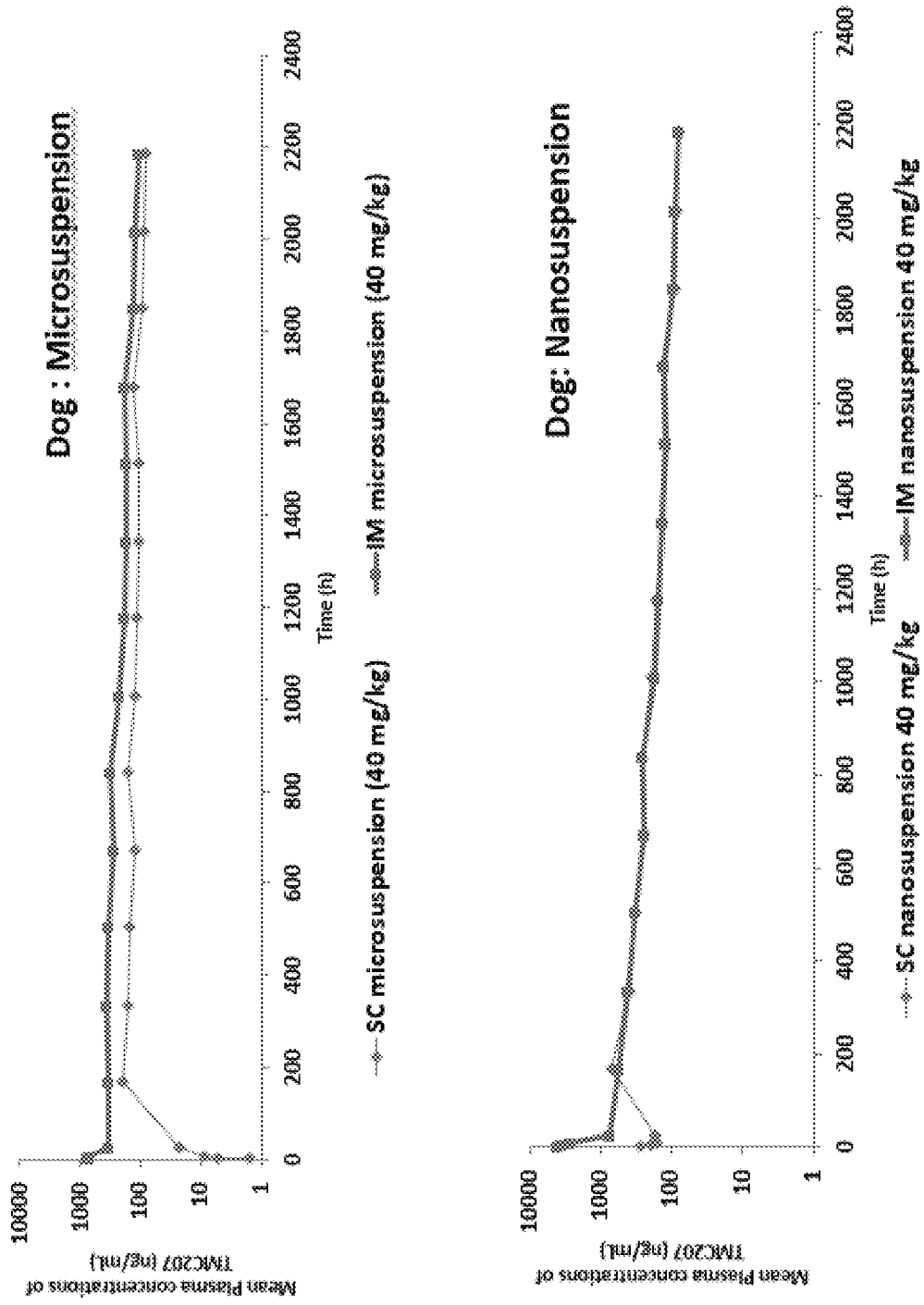

FIG. 7: "Plasma kinetics of TMC207 in male beagle dogs when administered IM or SC with 200 mg/ml micro-formulation (see Example 1, Formulation 1B) at a dose of 40 mg/kg" and "Plasma kinetics of TMC207 in male beagle dogs when administered IM or SC with 200 mg/ml nano-formulation (see Example 1, Formulation 1A) at a dose of 40 mg/kg"

DETAILED DESCRIPTION OF THE INVENTION

The compound used in the invention is the compound TMC207, also referred to as bedaquiline.

Bedaquiline can be used in its non-salt form or as a suitable pharmaceutically acceptable salt form, such as an acid addition salt form or base addition salt form. In an embodiment, bedaquiline is in its non-salt form in compositions of the invention.

The pharmaceutically acceptable acid addition salts are defined to comprise the therapeutically active non-toxic acid addition salt forms which bedaquiline is able to form. Said acid addition salts can be obtained by treating the free form of bedaquiline with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid. In particular, the fumarate salt is considered, given that this is the form employed in the already-marketed product Sirturo®.

Possible therapeutically active non-toxic base addition salt forms may be prepared by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which bedaquiline as well as the salts thereof, are able to form. Such solvates are, for example, hydrates and alcoholates.

Whenever reference to bedaquiline (or TMC207) is employed herein, we refer to the single stereoisomeric form that is employed in the marketed product Sirturo®, and which is disclosed in WO2004/011436 as an antimycobacterial agent.

It has been found that the physico-chemical properties of bedaquiline allow for the manufacture of micro- or nanoparticle suspensions that have unique pharmacokinetic properties in that they can be used for the long term treatment of a pathogenic mycobacterial infection as well as in the long term prevention of a pathogenic mycobacterial infection and to this purpose only a limited number of drug administrations is required. This is beneficial in terms of pill-burden as well as patient compliance with the prescribed dose regimen.

As used herein the term "treatment of a pathogenic mycobacterial infection" relates to the treatment of a subject being infected with a pathogenic mycobacterial infection.

The term "prevention of a pathogenic mycobacterial infection" relates to the prevention or avoidance of a subject becoming infected with a pathogenic mycobacterial infection. The source of infection can be various, for instance a material containing a pathogenic mycobacterial infection.

The terms "therapeutically effective amount", "an amount, effective in preventing a pathogenic mycobacterial infection", and similar terms, refer to amounts, or concentrations, of the compositions of the invention (or amounts/concentrations of active ingredient bedaquiline within such compositions) that result in efficacious plasma levels. With "efficacious plasma levels" it is meant those plasma levels of bedaquiline that provide effective treatment or effective prevention of a pathogenic mycobacterial infection. This is because amount/dose/administration given may be linked to the desired exposure levels or desired plasma levels for the effective treatment/prevention, for instance as described herein (see e.g. the examples).

The term "subject" in particular relates to a human being.

The term "micro- or nanoparticles" refers to particles in the micrometer or nanometer range. The size of the particles should be below a maximum size above which administration by subcutaneous or intramuscular injection becomes impaired or is even no longer possible. Said maximum size depends for example on the limitations imposed by the needle diameter or by adverse reactions of the body to large particles, or both. In one embodiment, the pharmaceutical compositions of the invention comprise bedaquiline in microparticle form. In another embodiment, the pharmaceutical compositions of the invention comprise bedaquiline in nanoparticle form. The average effective particle size of the micro- or nanoparticles of the present invention may be below about 50 µm, or below about 20 µm, or below about 10 µm, or below about 1000 nm, or below about 500 nm, or below about 400 nm, or below about 300 nm, or below about 200 nm. The lower limit of the average effective particle size may be low, e.g. as low as about 100 nm or as low as about 50 nm. In one embodiment, the average effective particle size is in the range of about 50 nm to about 50 µm, or about 50 nm to about 20 µm, or about 50 nm to about 10 µm, or about 50 nm to about 1000 nm, or about 50 nm to about 500 nm, or about 50 nm to about 400 nm, or about 50 nm to about 300 nm, or about 50 nm to about 250 nm, or about 100 nm to about 250 nm, or about 150 nm to about 220 nm, or 100 to about 200 nm, or about 150 nm to about 200 nm, e.g. about 130 nm, or about 150 nm. For instance, both after preparation and after a period of time of up to 3 months (e.g. when stored at temperatures of about 5° C., 25° C. and 40° C.) generally:
  the micro-suspensions may have, in an embodiment, a D90 of between about 3 and 10 µm (e.g. about 3.5, 4 or 5 µm) and a D50 of between about 2 and 4 µm (e.g. about 3 µm)
  the nano-suspensions may have, in an embodiment, a D90 of between about 0.5 and 1.5 µm (e.g. about, or less than 1 µm or about, or less than about 1000 nm) and a D50 of between about 0.1 and 0.5 µm (e.g. about, or less than, about 0.3 µm, or less than about 300 nm).

In an embodiment, the micro-particles are employed, wherein the average effective particle size, as measured by D10, D50 and/or D90 (in an embodiment as measured by D50) is below about 50 µm, or below about 20 µm, and above about 0.1 µm (100 nm). In an embodiment the range for such micro-particles employed in the compositions of the invention is between about 20 µm and about 0.1 µm (in a further embodiment between about 15 µm, and above about 0.2 µm (200 nm) and in a further embodiment between about 10 µm, and above 0.5 µm (500 nm), for instance between about 10 µm, and above 1 µm or below about 1000 nm, or below about 500 nm, or below about 400 nm, or below about 300 nm, or below about 200 nm. The foregoing values are refer to measurements after preparation. They may also, however, in an embodiment, refer to measurements after a period of time up to 3 months (e.g. after 5 days, one week, two weeks, one month, two months or three months) and stored at various temperatures (e.g. at temperatures of about 5° C., 25° C. and 40° C.).

As used herein, the term average effective particle size has its conventional meaning as known to the person skilled in the art and can be measured by art-known particle size measuring techniques such as, for example, sedimentation field flow fractionation, photon correlation spectroscopy, laser diffraction or disk centrifugation. The average effective particle sizes mentioned herein may be related to volume distributions of the particles. In that instance, by "an effective average particle size of less than about 50 µm" it is meant that at least 50% of the volume of the particles has a particle size of less than the effective average of 50 µm, and the same applies to the other effective particle sizes mentioned. In a similar manner, the average effective particle sizes may be related to weight distributions of the particles but usually this will result in the same or about the same value for the average effective particle size.

The pharmaceutical compositions of the present invention provide release of the active ingredient bedaquiline over a prolonged period of time and therefore they can also be referred to as sustained or delayed release compositions. After administration, the compositions of the invention stay in the body and steadily release bedaquiline, keeping such levels of this active ingredient in the patient's system for a prolonged period of time, thereby providing, during said period, the appropriate treatment or prevention of a pathogenic mycobacterial infection. Because of the fact that the pharmaceutical compositions of the invention stay in the body and steadily release bedaquiline (and its active metabolite, referred to as M2 herein; see hereinafter, the methyl-substituted metabolite), they can be referred to as pharmaceutical compositions suitable as long-acting (or depot) formulations.

As used herein with the term "prolonged period of time", there is meant a term (or time period) that may be in the range of one week up to one year or up to two years, or a term in the range of one to two weeks, or two to three weeks, or three to four weeks, or a term in the range of one to two months, or two to three months, or three to four months, or three to six months, or six months to 12 months, or 12 months to 24 months, or a term that is in the range of several days, e.g. 7, 10 or 12 days, or several weeks, e.g. 2, 3 or 4 weeks, or one month, or several months, e.g. 2, 3, 4, 5 or six months or even longer, e.g. 7, 8, 9 or 12 months.

The pharmaceutical compositions of this invention may be applied in the long-term treatment or the long-term prevention of a pathogenic mycobacterial infection, or with other words they may be used in the treatment of a pathogenic mycobacterial infection, or in the prevention of a pathogenic mycobacterial infection, during a prolonged period of time. The compositions of the invention are effective in the treatment or prevention of a pathogenic mycobacterial infection for a prolonged period of time, for example for at least about one week or longer, or for about 1 month or longer. By the expression "effective for at least about one week or longer", one means that the plasma level of the active ingredient, bedaquiline (and/or its active metabolite M2), should be above a threshold value. In case of therapeutic application said threshold value is the lowest plasma level at which bedaquiline (and/or its active metabolite M2) provides effective treatment of a pathogenic mycobacterial infection. In case of application in the prevention of a pathogenic mycobacterial infection said threshold value is the lowest plasma level at which bedaquiline (and/or its active metabolite M2) is effective in preventing transmission of a pathogenic mycobacterial infection.

With "long term" for example as used in relation to "long term prevention of a pathogenic mycobacterial infection" or "long term treatment of a pathogenic mycobacterial infection", or similar terminology, there are meant terms that may be in the range of one week up to one year or up to two years, or longer, such as five or 10 years. In particular in the case of treatment of a pathogenic mycobacterial infection, such terms will be long, in the order of one to several months, one year or longer. Such terms may also be relatively short, in particular in the case of prevention. Shorter terms are those of several days, e.g. 7, 10 or 12 days, or several weeks, e.g. 2, 3 or 4 weeks, or one month, or several months, e.g. 2, 3, 4, 5 or six months or even longer, e.g. 7, 8, 9 or 12 months. In one embodiment the methods and uses in accordance with the present invention are for the prevention of a pathogenic mycobacterial infection during one month, or several months, e.g. 2, 3, 4, 5 or six months or even longer, e.g. 7, 8, 9 or 12 months.

The pharmaceutical compositions of the present invention can be administered at various time intervals. When used in the prevention of a pathogenic mycobacterial infection, the pharmaceutical compositions of this invention can be administered only once or a limited number of times such as twice, three, four, five or six times, or more. This may be recommendable where prevention is required during a limited period of time, such as the period during which there is a risk of infection.

The pharmaceutical compositions of the present invention can be administered at the time intervals mentioned above, such as at a time interval that is in the range of one week to one month, or in the range of one month to three months, or in the range of three months to six months, or in the range of six months to twelve months. In one embodiment, the pharmaceutical composition can be administered once every two weeks, or once every month, or once every three months. In another embodiment the time interval is in the range of one to two weeks, or two to three weeks, or three to four weeks, or the time interval is in the range of one to two months, or two to three months, or three to four months, or three to six months, or six months to 12 months, or 12 months to 24 months. The time interval may be at least one week, but may also be several weeks, e.g. 2, 3, 4, 5 or 6 weeks, or at time intervals of one month, or of several months, e.g. 2, 3, 4, 5 or 6 months or even longer, e.g. 7, 8, 9 or 12 months. In one embodiment, the pharmaceutical compositions of the present invention are administered at a time interval of one, two or three months. These longer periods between each administration of the pharmaceutical compositions of the invention provide further improvements in terms of pill burden and compliance. To further improve compliance, patients can be instructed to take their medication at a certain day of the week, where the composition is administered on a weekly schedule, or at a certain day of the month in case of a monthly schedule.

The length of the time intervals between each administration of a composition of the present invention may vary. For example said time intervals may be selected in function of the plasma levels. The intervals may be shorter where the plasma levels of bedaquiline (and/or its active metabolite M2) are deemed too low, e.g. when these approach the minimum plasma level specified hereinafter. The intervals may be longer where the plasma levels of bedaquiline (and/or its active metabolite M2) are deemed too high. In one embodiment, the compositions of the invention are administered at equal time intervals. The compositions may be administered without any interjacent additional administrations, or with other words, the compositions may be administered at particular points in time separated from one another by a time period of varying or equal length, e.g. a time period of at least one week, or any other time period specified herein, during which no further bedaquiline is administered. Having time intervals of the same length has the advantage that the administration schedule is simple, e.g. administration takes place at the same day in the week, or the same day in the month. Such administration schedule therefore involves limited "pill burden" thereby contributing beneficially to the patient's compliance to the prescribed dosing regimen.

The concentration (or "C") of bedaquiline (and/or its active metabolite M2) in the plasma of a subject treated therewith is generally expressed as mass per unit volume, typically nanograms per milliliter (ng/ml). For convenience, this concentration may be referred to herein as "plasma drug concentration" or "plasma concentration".

The dose (or amount) of bedaquiline administered, depends on the amount of bedaquiline in the pharmaceutical compositions of the invention, or on the amount of a given composition that is administered. Where higher plasma levels are desired, either or both of a composition of higher bedaquiline concentration, or more of a given composition, may be administered. This applies vice versa if lower plasma levels are desired. Also a combination of varying time intervals and varying dosing may be selected to attain certain desired plasma levels.

The dose (or amount) of bedaquiline administered also depends on the frequency of the administrations (i.e. the time interval between each administration). Usually, the dose will be higher where administrations are less frequent. All these parameters can be used to direct the plasma levels to desired values The dosing regimen also depends on whether prevention or treatment of the pathogenic mycobacterial infection is envisaged. In case of therapy, the dose of bedaquiline administered or the frequency of dosing, or both, are selected so that the plasma concentration of bedaquiline is kept above a minimum plasma level. The term "minimum plasma level" (or $C_{min}$) in this context refers to the plasma level of bedaquiline (and/or its active metabolite M2) that provides effective treatment of the pathogenic mycobacterial infection. In particular, the plasma level of bedaquiline (and/or its active metabolite M2) is kept at a level above a minimum plasma level of about 10 ng/ml, or above about 15 ng/ml, or above about 20 ng/ml, or above about 40 ng/ml. The plasma level of bedaquiline (and/or its active metabolite M2) may be kept above a minimum plasma level that is higher, for example above about 50 ng/ml, or above about 90 ng/ml, or above about 270 ng/ml, or above about 540 ng/ml. In one embodiment, the plasma level of bedaquiline (and/or its active metabolite M2) is kept above a level of about 13.5 ng/ml, or is kept above a level of about 20 ng/ml. Or the plasma level of bedaquiline (and/or its active metabolite M2) may be kept within certain ranges, in particular ranges starting from a minimum plasma level selected from those mentioned above and ending at a higher plasma levels selected from those mentioned above and selected from 500 ng/ml and 1000 ng/ml (e.g. from 10 to 15, 10 to 20, 10 to 40, etc., or from 15 to 20, or 15 to 40, or 15 to 90, etc., or 20 to 40, 20 to 90, or 20 to 270, etc., or 40 to 90, 40 to 270, or 40-540, etc., each time from about the indicated value in ng/ml to about the indicated value in ng/ml). In one embodiment said range is from about 10 to about 20, from about 20 to about 90, from 90 to 270, from 270 to 540, from 540 to 1000, each time from about the indicated value in ng/ml to about the indicated value in ng/ml.

The plasma levels of bedaquiline (and/or its active metabolite M2) should be kept above the above-mentioned minimum plasma levels because at lower levels the bacteria may no longer be sufficiently suppressed so that it can multiply with the additional risk of the emergence of mutations.

In the instance of prevention, the term "minimum plasma level" (or $C_{min}$) refers to the lowest plasma level of bedaquiline (and/or its active metabolite M2) that provides effective treatment/prevention of infection.

In particular, in the instance of prevention, the plasma level of bedaquiline (and/or its active metabolite M2) can be kept at a level above a minimum plasma level mentioned above in relation to therapy. However in prevention the plasma level of bedaquiline (and/or its active metabolite M2) can be kept at a lower level, for example at a level above about 4 ng/ml, or about 5 ng/ml, or about 8 ng/ml. The plasma levels of bedaquiline (and/or its active metabolite M2) should preferably be kept above these minimum plasma levels because at lower levels the drug may no longer be effective thereby increasing the risk of transmission of infection. Plasma levels of bedaquiline (and/or its active metabolite M2) may be kept at somewhat higher levels to have a safety margin. Such higher levels start from about 50 ng/ml or more. The plasma level of bedaquiline (and/or its active metabolite M2) can be kept at a level that is in the ranges mentioned above in relation to therapy, but where the lower limits include the plasma levels of about 4 ng/ml, or about 5 ng/ml, or about 8 ng/ml.

An advantage of bedaquiline (and/or its active metabolite M2) is that it may be used up to relatively high plasma levels without any significant side effects. The plasma concentrations of bedaquiline (and/or its active metabolite M2) may reach relatively high levels, but as with any drug should not exceed a maximum plasma level (or $C_{max}$), which is the plasma level where bedaquiline (and/or its active metabolite M2) causes significant side effects. Additionally, compound-release from the tissue should also be taken into account, which is not counted for within plasma levels. As used herein, the term "significant side effects" means that the side effects are present in a relevant patient population to an extend that the side effects affect the patients' normal functioning. In an embodiment, the amount and the frequency of administrations of bedaquiline (and/or its active metabolite M2) to be administered are selected such that the plasma concentrations are kept during a long term at a level comprised between a maximum plasma level (or $C_{max}$ as specified above) and a minimum plasma level (or $C_{min}$ as specified above).

In certain instances it may be desirable to keep the plasma levels of bedaquiline (and/or its active metabolite M2) at relatively low levels, e.g. as close as possible to the minimum plasma levels specified herein. This will allow reducing the frequency of the administrations and/or the quantity of bedaquiline (and/or its active metabolite M2) administered with each administration. It will also allow avoiding undesirable side effects, which will contribute to the acceptance of the dosage forms in most of the targeted population groups who are healthy people at risk of being infected and therefore are less inclined to tolerate side effects. The plasma levels of bedaquiline (and/or its active metabolite M2) may be kept at relatively low levels in the instance of prevention. One embodiment concerns uses or methods for prevention of infection, as specified above or hereinafter, wherein the minimum plasma level of bedaquiline (and/or its active metabolite M2) is as specified herein and the maximum plasma level is about equal to the lowest plasma level that causes the active ingredient to act therapeutically, also as specified herein.

In other embodiments, the plasma level of bedaquiline (and/or its active metabolite M2) is kept at a level below a lower maximum plasma level of about 10 ng/ml, more in particular about 15 ng/ml, further in particular about 20 ng/ml, still more in particular about 40 ng/ml. In a particular embodiment, the plasma level of bedaquiline (and/or its active metabolite M2) is kept below a level of about 13.5 ng/ml. In one embodiment, the plasma level of bedaquiline (and/or its active metabolite M2) is kept in an interval of the lower maximum blood level specified above, and the minimum plasma levels mentioned in relation to prevention. For example the plasma levels of bedaquiline (and/or its active metabolite M2) are kept below about 10 ng/ml and above a minimum level of about 4 ng/ml.

In other instances it may be desirable to keep the plasma levels of bedaquiline (and/or its active metabolite M2) at relatively higher levels, for example where there is a high risk of infection and more frequent and/or higher doses are not an issue. In these instances the minimum plasma level may be equal to the lowest plasma level of bedaquiline (and/or its active metabolite M2) that provides effective treatment of a pathogenic mycobacterial infection, such as the specific levels mentioned herein.

In the instance of prevention, the dose to be administered should be calculated on a basis of about 0.2 mg/day to about 50 mg/day, or 0.5 mg/day to about 50 mg/day, or of about 1 mg/day to about 10 mg/day, or about 2 mg/day to about 5 mg/day, e.g. about 3 mg/day. This corresponds to a weekly dose of about 1.5 mg to about 350 mg, in particular of about 3.5 mg to about 350 mg, in particular of about 7 mg to about 70 mg, or about 14 mg to about 35 mg, e.g. about 35 mg, or to a monthly dose of from 6 mg to about 3000 mg, in particular about 15 mg to about 1,500 mg, more in particular of about 30 mg to about 300 mg, or about 60 mg to about 150 mg, e.g. about 150 mg. Doses for other dosing regimens can readily be calculated by multiplying the daily dose with the number of days between each administration.

In the instance of therapy, the dose to be administered should be somewhat higher and should be calculated on a basis of about 1 mg/day to about 150 mg/day, or of about 2 mg/day to about 100 mg/day, or of about 5 mg/day to about 50 mg/day, or of about 10 mg/day to about 25 mg/day, e.g. about 15 mg/day. The corresponding weekly or monthly doses can be calculated as set forth above. For applications in prevention, the doses may be lower although the same dosing as for therapeutic applications may be used. In an embodiment, the dose/administration is given at monthly intervals or three-monthly or six-monthly intervals, with the total treatment duration being three, six or 12 months. In the instances where the dose/administration is monthly, three monthly or six-monthly, in an embodiment, the dose given (e.g. in human subjects) is calculated on the basis of a 400 mg daily dose given for 2 weeks. Hence, the total amount of bedaquiline given per dose may be about 5600 mg (e.g. in the range of 3000 and 8000 mg), but it may be up to one fifth of such an amount (e.g. in the range of 500 and 2000 mg, e.g. between about 1000 and 1500 mg).

In another embodiment, in the case of prevention or in particular therapy, the doses may also be expressed in mg/kg. For instance, in the examples, certain doses may be administered based on weight (of e.g. the mammal, and as shown in the examples here, in mouse) and hence doses between 1 mg/kg and 1000 mg/kg may be employed (e.g. 40 mg/kg, 80 mg/kg, 160 mg/kg, 320 mg/kg or 480 mg/kg may be employed) and such doses may remain effective for a period of 4 weeks, 8 weeks or 12 weeks (for example as shown in the examples). For instance, one dose may be taken every 4 weeks (effectively seen as a 12 week treatment regimen, i.e. three doses in total) or one single dose may be taken, which effectively provides sufficient treatment (e.g. as defined by reduction in CFUs, see examples) as may be evidenced by monitoring over a 12 week period. Hence, in an aspect, in order to treat the bacterial infection one dose may be taken (e.g. between 1 mg/kg and 1000 mg/kg, for instance between 2 mg/kg and 500 mg/kg) or one such dose may be taken every 4 weeks (e.g. two or three such doses may be taken). Such dose depends on the bacterial infection to be treated. For instance, in the treatment of latent tuberculosis or leprosy, lower doses may be required (compared to e.g. multi-drug resistant tuberculosis) given that a lower amount of bedaquiline is required to control the bacteria. An example of this is described hereinafter (Example 3), wherein it is indicated that in mice one dose of 160 mg/kg may sufficiently reduce CFUs in the mouse model of latent tuberculosis infection—it was also seen that two or three doses of 160 mg/kg (the second and the third doses administered at 4 and 8 weeks, respectively) were also effective in that model.

It has been found that, once administered, the plasma levels of bedaquiline (and/or its active metabolite M2) are more or less stable, i.e. they fluctuate within limited margins. The plasma levels have been found to approach more or less a steady state mode or to approximate more or less a zero order release rate during a prolonged period of time. By "steady state" is meant the condition in which the amount of drug present in the plasma of a subject stays at more or less the same level over a prolonged period of time. The plasma levels of bedaquiline (and/or its active metabolite M2) generally do not show any drops below the minimum plasma level at which the drug is effective. The term "stays at more or less the same level" does not exclude that there can be small fluctuations of the plasma concentrations within an acceptable range, e.g. fluctuations within a range of about ±30%, or about ±20%, or about ±10%, or about ±10%.

In some instances there may be an initial plasma concentration peak after administration, after which the plasma levels achieve a "steady-state", as mentioned hereinafter.

The compositions of the invention show good local tolerance and ease of administration. Good local tolerance relates to minimal irritation and inflammation at the site of injection; ease of administration refers to the size of needle and length of time required to administer a dose of a particular drug formulation. In addition, the compositions of the invention show good stability and have an acceptable shelf life.

The micro- or nanoparticles of the present invention have a surface modifier adsorbed on the surface thereof. The function of the surface modifier is to act as a wetting agent as well as a stabilizer of the colloidal suspension.

In one embodiment, the micro- or nanoparticles in the compositions of the invention mainly comprise crystalline bedaquiline or a salt thereof; and a surface modifier, the combined amount of which may at least comprise about 50%, or at least about 80%, or at least about 90%, or at least about 95%, or at least about 99% of the micro- or nano particles. As indicated herein, in an embodiment, bedaquiline is in its non-salt form (or in its "free form") and in a further embodiment it is in a crystalline non-salt (or free) form. In this respect, as mentioned herein, bedaquiline may be prepared as such using the procedures described in international patent application WO 2004/011436 (or in WO 2006/125769, which describes an optical resolution with a chiral reagent). Following such procedure, the bedaquiline is obtained by precipitation from toluene/ethanol and it is indicated that the product crystallises. Such form of bedaquiline may be used in the preparation of the compositions of the invention and, further, such form may be a single crystalline polymorph with the following characterising features:

(i) a melting endotherm at 181.5° C. (endotherm onset) and DSC curve showing melting of the product at about 182.5° C. (immediately followed by decomposition; measured by differential scanning calorimetry (DSC) by transfer of about 3 mg of compound into a standard aluminum TA-Instrument sample pan, sample pan closed with the appropriate coer and DSC curve recorded on a TA-Instruments Q2000 MTDSC equipped with a RCS cooling unit using the following parameters—initial temperature 25° C.; heating range 10° C./min; final temperature 300° C., nitrogen flow 50 ml/min);

(ii) infrared (IR) spectrum peaks at inter alia about 1600 $cm^{-1}$, about 1450 $cm^{-1}$, about 1400 $cm^{-1}$, about 1340 $cm^{-1}$, and about 1250 $cm^{-1}$ (where a sample is analysed using a suitable microATR accessory deploying 32 scans, 1 $cm^{-1}$ resolution, Thermo Nexus 670 FTIR spectrometer, a DTGS with KBr windows detector, Ge on KBr beamsplitter and a micro ATR accessory (Harrick Split Pea with Si crystal); and/or (iii) X-ray powder diffraction (XRPD) with characteristic peaks at about 11.25° 2-Theta, about 18° 2-Theta, about 18.5° 2-Theta, about 19° 2-Theta, about 20.25° 2-Theta, about 21.25° 2-Theta, about 22.25° 2-Theta, about 24.5° 2-Theta and about 27° 2-Theta, showing diffraction peaks without the presence of a halo indicating crystallinity of the product (where the analysis was carried out on a PANalytical (Philips) X'PertPRO MPD diffractometer, and the instrument is equipped with a Cu LFF X-ray tube and the compound was spread on a zero background sample holder; the Instrument Parameters were: generator voltage—45 kV; generator amperage—40 mA; geometry—Bragg-Brentano; stage—spinner stage; scan mode—continuous; scan range 3 to 50° 2θ; step size 0.02°/step; counting time 30 sec/step; spinner revolution time—1 sec; radiation type CuKα).

Hence, in an embodiment, the bedaquiline employed in a process to prepare compositions of the invention (i.e. before conversion to micro/nano-particles) is a crystalline form (e.g. of the specific form characterised above). In a further embodiment of the invention, the bedaquiline employed in the compositions of the invention (i.e. after conversion to micro/nano-particles, for instance by milling) is also in a crystalline form (e.g. of the specific form characterised above).

In a further aspect, the present invention is concerned with a pharmaceutical composition for administration by intramuscular or subcutaneous injection, comprising a therapeutically effective amount of bedaquiline, or a pharmaceutically acceptable salt thereof, in the form of a suspension of particles consisting essentially of:
(1) bedaquiline, or a pharmaceutically acceptable salt thereof in micro- or nanoparticle form, having a surface modifier adsorbed to the surface thereof; and
(2) a pharmaceutically acceptable aqueous carrier; wherein the active ingredient is suspended.

Suitable surface modifiers can be selected from known organic and inorganic pharmaceutical excipients, including various polymers, low molecular weight oligomers, natural products and surfactants. Particular surface modifiers include nonionic and anionic surfactants. Representative examples of surface modifiers include gelatin, casein, lecithin, salts of negatively charged phospholipids or the acid form thereof (such as phosphatidyl glycerol, phosphatidyl inosite, phosphatidyl serine, phosphatic acid, and their salts such as alkali metal salts, e.g. their sodium salts, for example egg phosphatidyl glycerol sodium, such as the product available under the tradename Lipoid™ EPG), gum acacia, stearic acid, benzalkonium chloride, polyoxyethylene alkyl ethers, e.g., macrogol ethers such as cetomacrogol 1000, polyoxyethylene castor oil derivatives; polyoxyethylene stearates, colloidal silicon dioxide, sodium dodecylsulfate, carboxymethylcellulose sodium, bile salts such as sodium taurocholate, sodium desoxytaurocholate, sodium desoxycholate; methylcellulose, hydroxyethylcellulose, hydroxypropylcellulose, hydroxypropyl-methylcellulose, magnesium aluminate silicate, polyvinyl alcohol (PVA), poloxamers, such as Pluronic™ F68, F108 and F127 which are block copolymers of ethylene oxide and propylene oxide; tyloxapol; Vitamin E-TGPS (α-tocopheryl polyethylene glycol succinate, in particular α-tocopheryl polyethylene glycol 1000 succinate); poloxamines, such as Tetronic™ 908 (T908) which is a tetrafunctional block copolymer derived from sequential addition of ethylene oxide and propylene oxide to ethylenediamine; dextran; lecithin; dioctyl ester of sodium sulfosuccinic acid such as the products sold under the tradename Aerosol OT™ (AOT); sodium lauryl sulfate (Duponol™ P); alkyl aryl polyether sulfonate available under the tradename Triton™ X-200; polyoxyethylene sorbitan fatty acid esters (Tweens™ 20, 40, 60 and 80); sorbitan esters of fatty acids (Span™ 20, 40, 60 and 80 or Arlacel™ 20, 40, 60 and 80); polyethylene glycols (such as those sold under the tradename Carbowax™ 3550 and 934); sucrose stearate and sucrose distearate mixtures such as the product available under the tradename Crodesta™ F110 or Crodesta™ SL-40; hexyldecyl trimethyl ammonium chloride (CTAC); polyvinylpyrrolidone (PVP). If desired, two or more surface modifiers can be used in combination.

Particular surface modifiers are selected from poloxamers, α-tocopheryl polyethylene glycol succinates, polyoxyethylene sorbitan fatty acid esters, and salts of negatively charged phospholipids or the acid form thereof. More in particular the surface modifiers are selected from Pluronic™ F108, Vitamin E TGPS, Tween™ 80, and Lipoid™ EPG (and, in a particular embodiment, it is Vitamin E TPGS). One or more of these surface modifiers may be used. Pluronic™ F108 corresponds to poloxamer 338 and is the polyoxyethylene, polyoxypropylene block copolymer that conforms generally to the formula HO—[$CH_2CH_2O$]$_x$—[$CH(CH_3)CH_2O$]$_y$—[$CH_2CH_2O$]$_z$—H in which the average values of x, y and z are respectively 128, 54 and 128. Other commercial names of poloxamer 338 are Hodag Nonionic™ 1108-F and Synperonic™ PE/F108. In one embodiment, the surface modifier comprises a combination of a polyoxyethylene sorbitan fatty acid ester and a phosphatidyl glycerol salt (in particular egg phosphatidyl glycerol sodium).

The optimal relative amount of bedaquiline in relation to the surface modifier depends on the surface modifier selected, the specific surface area of the bedaquiline suspension which is determined by the average effective particle size and the bedaquiline concentration, the critical micelle concentration of the surface modifier if it forms micelles, etc. The relative amount (w/w) of bedaquiline to the surface modifier preferably is in the range of 1:2 to about 20:1, in particular in the range of 1:1 to about 10:1, e.g. about 4:1.

The particles of this invention can be prepared by means of micronization/particle size reduction/nanonization by mechanical means and by controlled precipitation from a supersaturated solution, or by using supercritical fluids such as in the GAS technique ("gas anti-solvent"), or any combination of such techniques. In one embodiment a method is used comprising the steps of dispersing bedaquiline in a liquid dispersion medium and applying mechanical means in the presence of grinding media to reduce the particle size of bedaquiline to an average effective particle size of less than about 50 μm, in particular less than about 1,000 nm. The particles can be reduced in size in the presence of a surface modifier.

A general procedure for preparing the particles of this invention comprises
(a) obtaining bedaquiline in micronized form;
(b) adding the micronized bedaquiline to a liquid medium to form a premix/predispersion; and
(c) subjecting the premix to mechanical means in the presence of a grinding medium to reduce the average effective particle size.

Bedaquiline in micronized form is prepared using techniques known in the art. It is preferred that the average effective particle size of the bedaquiline active agent in the predispersion be less than about 100 μm as determined by sieve analysis. Where the average effective particle size of the micronized bedaquiline is greater than about 100 μm, it is preferred that the particles of the bedaquiline compound be reduced in size to less than 100 μm (for example to a size or size range as described herein).

The micronized bedaquiline can then be added to a liquid medium in which it is essentially insoluble to form a predispersion. The concentration of bedaquiline in the liquid medium (weight by weight percentage) can vary widely and depends on the selected surface modifier and other factors. Suitable concentrations of bedaquiline in compositions vary between about 0.1% to about 60%, or between about 1% to about 60%, or between about 10% to about 50%, or between about 10% to about 30%, e.g. about 10%, 20% or 30% (each % in this paragraph relating to w/v).

The premix can be used directly by subjecting it to mechanical means to reduce the effective average effective particle size in the dispersion to less than 2,000 nm. It is preferred that the premix be used directly when a ball mill is used for attrition. Alternatively, bedaquiline and, optionally, the surface modifier, can be dispersed in the liquid medium using suitable agitation such as, for example, a roller mill, until a homogeneous dispersion is achieved.

The mechanical means applied to reduce the effective average effective particle size of bedaquiline conveniently can take the form of a dispersion mill. Suitable dispersion mills include a ball mill, an attritor/attrition mill, a vibratory mill, a planetary mill, media mills, such as a sand mill and a bead mill. A media mill is preferred due to the relatively shorter milling time required to provide the desired reduction in particle size. The beads preferably are $ZrO_2$ beads. For instance, for the nanoparticles, the ideal bead size is about 0.5 mm and, for the microparticles, the ideal bead size is about 2 mm.

The grinding media for the particle size reduction step can be selected from rigid media preferably spherical or particulate in form having an average size less than 3 mm and, more preferably, less than 1 mm (as low as 200 μm beads). Such media desirably can provide the particles of the invention with shorter processing times and impart less wear to the milling equipment. Examples of grinding media are $ZrO_2$ such as 95% $ZrO_2$ stabilized with magnesia or stabilized with yttrium, zirconium silicate, glass grinding media, polymeric beads, stainless steel, titania, alumina and the like. Preferred grinding media have a density greater than 2.5 $g/cm^3$ and include 95% $ZrO_2$ stabilized with magnesia and polymeric beads.

The attrition time can vary widely and depends primarily upon the particular mechanical means and processing conditions selected. For rolling mills, processing times of up to two days or longer may be required.

The particles should be reduced in size at a temperature that does not significantly degrade the bedaquiline compound. Processing temperatures of less than 30 to 40° C. are ordinarily preferred. If desired, the processing equipment may be cooled with conventional cooling equipment. The method is conveniently carried out under conditions of ambient temperature and at processing pressures, which are safe and effective for the milling process.

The pharmaceutical compositions according to the present invention contain an aqueous carrier that preferably is pharmaceutically acceptable. Said aqueous carrier comprises sterile water optionally in admixture with other pharmaceutically acceptable ingredients. The latter comprise any ingredients for use in injectable formulations. Such ingredients are optional. These ingredients may be selected from one or more of a suspending agent, a buffer, a pH adjusting agent, a preservative, an isotonizing agent, and the like ingredients. In one embodiment, said ingredients are selected from one or more of a suspending agent, a buffer, a pH adjusting agent, and optionally, a preservative and an isotonizing agent. Particular ingredients may function as two or more of these agents simultaneously, e.g. behave like a preservative and a buffer, or behave like a buffer and an isotonizing agent.

Suitable optional buffering agents and pH adjusting agents should be used in amount sufficient to render the dispersion neutral to very slightly basic (up to pH 8.5), preferably in the pH range of 7 to 7.5. Particular buffers are the salts of week acids. Buffering and pH adjusting agents that can be added may be selected from tartaric acid, maleic acid, glycine, sodium lactate/lactic acid, ascorbic acid, sodium citrates/citric acid, sodium acetate/acetic acid, sodium bicarbonate/carbonic acid, sodium succinate/succinic acid, sodium benzoate/benzoic acid, sodium phosphates, tris(hydroxymethyl)aminomethane, sodium bicarbonate/sodium carbonate, ammonium hydroxide, benzene sulfonic acid, benzoate sodium/acid, diethanolamine, glucono delta lactone, hydrochloric acid, hydrogen bromide, lysine, methanesulfonic acid, monoethanolamine, sodium hydroxide, tromethamine, gluconic, glyceric, gluratic, glutamic, ethylene diamine tetraacetic (EDTA), triethanolamine, including mixtures thereof. In an embodiment, the compositions of the invention do not contain a buffering agent.

Suitable optional preservatives comprise antimicrobials and anti-oxidants which can be selected from the group consisting of benzoic acid, benzyl alcohol, butylated hydroxyanisole (BHA), butylated hydroxytoluene (BHT), chlorbutol, a gallate, a hydroxybenzoate, EDTA, phenol, chlorocresol, metacresol, benzethonium chloride, myristyl-γ-piccolinium chloride, phenylmercuric acetate and thimerosal. Radical scavengers include BHA, BHT, Vitamin E and ascorbyl palmitate, and mixtures thereof. Oxygen scavengers include sodium ascorbate, sodium sulfite, L-cysteine, acetylcysteine, methionine, thioglycerol, acetone sodium bisulfate, isoacorbic acid, hydroxypropyl cyclodextrin. Chelating agents include sodium citrate, sodium EDTA and malic acid. In an embodiment of the invention, the compositions of the invention do not contain a perseverative.

An isotonizing agent or isotonifier may be present to ensure isotonicity of the pharmaceutical compositions of the present invention, and includes sugars such as glucose, dextrose, sucrose, fructose, trehalose, lactose; polyhydric sugar alcohols, preferably trihydric or higher sugar alcohols, such as glycerin, erythritol, arabitol, xylitol, sorbitol and mannitol. Alternatively, sodium chloride, sodium sulfate, or other appropriate inorganic salts may be used to render the solutions isotonic. These isotonifiers can be used alone or in combination. The suspensions conveniently comprise from 0 to 10% (w/v), in particular 0 to 6% of isotonizing agent. Of interest are nonionic isotonifiers, e.g. glucose, as electrolytes may affect colloidal stability. In an embodiment of the invention, the compositions of the invention contain a isotonizing agent or isotonifier, which, in a further embodiment is a nonionic isotonifier, such as a suitable sugar such as mannitol.

A desirable feature for a pharmaceutical composition of the invention relates to the ease of administration. The viscosity of the pharmaceutical compositions of the invention should be sufficiently low to allow administration by injection. In particular they should be designed so that they can be taken up easily in a syringe (e.g. from a vial), injected through a fine needle (e.g. a 20 G 1½, 21 G 1½, 22 G 2 or 22 G 1¼ needle) in not too long a time span. In one embodiment the viscosity of the compositions of the invention is below about 75 mPa·s, or below 60 mPa·s. Aqueous suspensions of such viscosity or lower usually meet the above-mentioned criteria.

Ideally, the aqueous suspensions according to the present invention will comprise as much bedaquiline (or pharmaceutically acceptable salt thereof) as can be tolerated so as to keep the injected volume to a minimum, in particular from 3 to 70% (w/v), or from 3 to 60% (w/v), or from 3 to 40% (w/v), or from 10 to 40% (w/v), of bedaquiline (or pharmaceutically acceptable salt thereof). In one embodiment the aqueous suspensions of the invention contain about 50%-70% (w/v) of bedaquiline (or pharmaceutically acceptable salt thereof), or about 40%-60% (w/v) of bedaquiline (or pharmaceutically acceptable salt thereof), or about 30%-50% (w/v) of bedaquiline (or pharmaceutically acceptable salt thereof).

In one embodiment, the aqueous suspensions may comprise by weight, based on the total volume of the composition:
(a) from 10% to 70% (w/v), or from 20% to 60% (w/v), or from 20% to 50% (w/v), or from 20% to 40% (w/v) of bedaquiline (or pharmaceutically acceptable salt thereof);
(b) from 0.5% to 20%, or from 2% to 15% or 20% (w/v), or from 5% to 15% (w/v) of a wetting agent;
(c) from 0% to 10%, or from 0% to 5%, or from 0% to 2%, or from 0% to 1% of one or more buffering agents;
(d) from 0% to 20%, or from 2% to 15% or 20% (w/v), or from 5% to 15% (w/v) of a isotonizing agent (e) from 0% to 2% (w/v) preservatives; and
(f) water for injection q.s. ad 100%.

In one embodiment, the aqueous suspensions may comprise by weight, based on the total volume of the composition:
(a) from 3% to 50% (w/v), or from 10% to 40% (w/v), or from 10% to 30% (w/v), of bedaquiline (or pharmaceutically acceptable salt thereof);
(b) from 0.5% to 10%, or from 0.5% to 2% (w/v) of a wetting agent;
(c) from 0% to 10%, or from 0% to 5%, or from 0% to 2%, or from 0% to 1% of one or more buffering agents;
(d) from 0% to 10%, or from 0% to 6% (w/v) of a isotonizing agent
(e) from 0% to 2% (w/v) preservatives; and
(f) water for injection q.s. ad 100%.

To the suspensions may optionally be added an amount of acid or base to bring the pH to a value of about pH 7. Suitable acids or bases are any of those that are physiologically acceptable, e.g. HCl, HBr, sulfuric acid, alkali metal hydroxides such as NaOH. In an embodiment, such acid or base need not be added to the compositions of the invention.

The administration of bedaquiline (or pharmaceutically acceptable salt thereof) as in the present invention may suffice to treat a pathogenic mycobacterial infection although in a number of cases it may be recommendable to co-administer other anti-TB drugs.

In certain instances, the treatment of a pathogenic mycobacterial infection may be limited to only the administration of a composition of bedaquiline (and/or its metabolite thereof) in accordance with this invention, i.e. as monotherapy without co-administration of further anti-TB drugs. This option may be recommended, for example, for certain mycobacterial infections where a low concentration of the active ingredient may treat the bacteria (e.g. for latent/dormant TB or for *Mycobacterium leprae*).

In a further aspect the present invention relates to the use of a pharmaceutical composition comprising an effective amount of bedaquiline or a pharmaceutically acceptable salt thereof, in accordance with the present invention, for the manufacture of a medicament for maintenance therapy of a subject being infected with a pathogenic mycobacterial infection, wherein the composition is administered or is to be administered intermittently at a time interval that is in the range of one week to one year, or one week to two years.

Thus in a further aspect, the present invention provides a method for the long term treatment of a patient being infected with a pathogenic mycobacterial infection, said method comprising
(i) the treatment of said patient with a combination of anti-TB drugs; followed by
(ii) the intermittent administration of a pharmaceutical composition comprising an effective amount of bedaquiline or a pharmaceutically acceptable salt thereof, in accordance with the present invention, wherein the composition is administered at a time interval of at least one week.

Where, the treatment is directed towards *Mycobacterium leprae*, then again the treatment regime might be given as monotherapy or in combination with existing drugs useful for the treatment of *Mycobacterium leprae* (e.g. rifapentin). The composition of the invention might be administered by injection once, or up to three times, e.g. as monthly intervals. Advantages are associated with compliance, no resistance by avoiding dapsone, no stigma by avoiding clofazimine.

The present invention also concerns a pharmaceutical composition as described hereinbefore for use as a medicament in the treatment or prophylaxis of a pathogenic mycobacterial infection.

In addition, the present invention concerns the use of a pharmaceutical composition as described herein for the preparation of a medicament for the prophylaxis or treatment of a pathogenic mycobacterial infection.

The present invention further concerns a method of treating a subject infected with a pathogenic mycobacterial infection, said method comprising the administration of a therapeutically effective amount of a pharmaceutical composition as described herein.

As used herein, the word "substantially" does not exclude "completely" e.g. a composition which is "substantially free" from Y may be completely free from Y. Where necessary, the word "substantially" may be omitted from the definition of the invention. The term "about" in connection with a numerical value is meant to have its usual meaning in the context of the numerical value. Where necessary the word "about" may be replaced by the numerical value ±10%, or ±5%, or ±2%, or ±1%. All documents cited herein are incorporated by reference in their entirety.

The following examples are intended to illustrate the present invention and should not be construed as limiting the invention thereto.

Example 1: Preparation of Micro- and Nano-Suspensions

The active ingredient bedaquiline may be used as such or may be converted into a pharmaceutically acceptable salt thereof, such as a fumarate salt (for example the form used in the marketed product Sirturo®). Where referred to herein, bedaquiline is used in its non-salt form unless otherwise specified.

The prototype of the bedaquiline formulation is as follows:

Preparation of 200 and 100 mg/mL nano- and micro-suspensions.

Materials Used:
Zirconium beads 0.5 mm (to aid process)
Sterile water for injection (Viaflo)
Bedaquiline (not milled/ground)
Tocopheryl PEG 1000 succinate—an excipient
Zirconium beads 2 mm (to aid process)
Mannitol (parenteral)—an excipient Glass bottles and $ZrO_2$ beads (either 0.5 mm or 2 mm, depending on the desired nano- or micro-suspensions), used as the milling media, were sterilized in an autoclave. The drug substance (quantity depending on the formulation to be prepared; see e.g. formulation/suspension below) was put into the glass bottle as well as a solution of Tocopheryl PEG 1000 succinate in water (quantity depending on the concentration required/desired; see e.g. formulation/suspension below) for injection. $ZrO_2$-beads with an average particle size of 500 μm or 2 mm (depending on whether a micro- or nano-suspension is required/desired) were added. The bottle was placed on a roller mill. The suspension was micronized/nanonized at 100 rpm for a period of time up to 72 hours. For instance, micronizing may be performed at 100 rpm for a period of 3 hours (or up to 3 hours) and nanonizing may be performed at 100 rpm for a period of up to 46 hours (e.g. about 40 hours). At the end of the milling process the concentrated micro- or nano-suspension was removed with a syringe and filled into vials. The resulting formulations (based on the nano-suspension and micro-suspension) are described in the following tables. Determination of the concentration was done by HPLC/UV. If needed, a dilution was made to a final concentration of 200 mg/ml of active ingredient bedaquiline. The resulting suspension was shielded from light. Other concentrations were also made and tested, including 300 mg/ml and 100 mg/ml nano- and micro-formulations.

Such formulations were (and will be) dosed intramuscular and subcutaneous in animals for PK study to investigate a possible long-acting effect (e.g. in treatment of leprosy). Physical stability of the suspensions will be followed up by measuring particle size after different storage conditions.

Certain embodiments of the formulation(s) have the following features:
  Micro-suspension by using 2 mm Zr beads
  Milling at 200 mg/mL (otherwise the concentration may be too high, e.g. with 300 mg/ml)
  Longer milling, resulting in nano-suspension
  A suitable surface modifier, for instance selected based on physical stability, e.g. in one embodiment it is TPGS, and, in another embodiment it is Tween Examples of Bedaquiline Micro- and Nano-Suspensions 200 mg/ml Nano- and Micro-Suspension Referred to Herein as Example 1A (Nano) and Example 1B (Micro)

|  | mg/ml |
|---|---|
| Bedaquiline | 200 |
| TPGS | 50 |
| Mannitol | 50 |
| Sterile water for injection | q.s. |

100 mg/ml Nano- and Micro-Suspension Referred to Herein as Example 1C (Nano) and Example 1D (Micro)

|  | mg/ml |
|---|---|
| Bedaquiline | 100 |
| TPGS | 25 |
| Mannitol | 50 |
| Sterile water for injection | q.s. |

Particle Size Distribution (PSD) of the Above Formulations
  Where applicable, ND=not determined
PSD for 200 mg/ml micro-suspension (Example 1B)

| Storage temperature (° C.) | Storage time | D10 (μm) | D50 (μm) | D90 (μm) |
|---|---|---|---|---|
| After preparation |  | 1.316 | 3.283 | 9.623 |
| 5 | 3 days | 1.256 | 2.539 | 5.991 |
|  | 14 days | 1.142 | 2.582 | 7.386 |
|  | 1 month | 1.157 | 2.423 | 5.850 |
|  | 3 months | 1.065 | 2.225 | 5.141 |
| 25 | 3 days | 1.150 | 2.348 | 5.447 |
|  | 14 days | 1.073 | 2.308 | 5.824 |
|  | 1 month | 1.098 | 2.322 | 5.665 |
|  | 3 months | 1.178 | 2.452 | 5.826 |
| 40 | 3 days | 1.110 | 2.227 | 4.913 |
|  | 14 days | 1.054 | 2.211 | 5.115 |
|  | 1 month | 1.182 | 2.254 | 4.626 |
|  | 3 months | 0.998 | 1.89 | 3.734 |

PSD for 200 mg/ml nano-suspension (Example 1A)

| Storage temperature (° C.) | Storage time | D10 (μm) | D50 (μm) | D90 (μm) |
|---|---|---|---|---|
| After preparation |  | 0.074 | 0.175 | 1.693 |
| 5 | 3 days | 0.076 | 0.185 | 1.920 |
|  | 14 days | 0.081 | 0.219 | 8.995 |
|  | 1 month | 0.075 | 0.176 | 1.281 |
|  | 3 months | 0.076 | 0.183 | 1.884 |
| 25 | 3 days | 0.111 | 41.364 | 226.147 |
|  | 14 days | ND | ND | ND |
|  | 1 month | ND | ND | ND |
|  | 3 months | ND | ND | ND |
| 40 | 3 days | 0.097 | 0.483 | 168.316 |
|  | 14 days | 0.1 | 0.642 | 240.375 |
|  | 1 month | 0.089 | 0.294 | 63.986 |
|  | 3 months | 0.088 | 0.274 | 4.279 |

PSD for 100 mg/ml micro-suspension (Example 1D)

| Storage temperature (° C.) | Storage time | D10 (μm) | D50 (μm) | D90 (μm) |
|---|---|---|---|---|
| After preparation |  | 1.267 | 2.557 | 6.236 |
| 5 | 3 days | 1.157 | 2.376 | 5.506 |
|  | 14 days | 0.125 | 0.320 | 0.993 |
|  | 1 month | 1.1 | 2.337 | 5.625 |
|  | 3 months | 1.048 | 2.236 | 5.269 |
| 25 | 3 days | 0.697 | 1.906 | 4.324 |
|  | 14 days | 0.151 | 1.770 | 4.351 |
|  | 1 month | 0.171 | 1.797 | 4.253 |
|  | 3 months | 1.104 | 2.266 | 5.142 |
| 40 | 3 days | 0.547 | 1.657 | 3.502 |
|  | 14 days | 0.203 | 1.709 | 3.881 |
|  | 1 month | 1.016 | 1.996 | 4.199 |
|  | 3 months | 1.025 | 1.936 | 3.867 |

PSD for 100 mg/ml nano-suspension (Example 1C)

| Storage temperature (° C.) | Storage time | D10 (μm) | D50 (μm) | D90 (μm) |
|---|---|---|---|---|
| After preparation |  | 0.072 | 0.159 | 0.576 |
| 5 | 3 days | 0.074 | 0.173 | 0.765 |
|  | 14 days | 0.080 | 0.213 | 7.889 |
|  | 1 month | 0.075 | 0.177 | 0.780 |
|  | 3 months | 0.074 | 0.172 | 0.919 |
| 25 | 3 days | 0.076 | 0.181 | 0.872 |
|  | 14 days | 0.080 | 0.202 | 1.351 |
|  | 1 month | 0.080 | 0.203 | 1.673 |
|  | 3 months | 0.083 | 0.222 | 1.691 |
| 40 | 3 days | 0.077 | 0.187 | 1.017 |
|  | 14 days | 0.082 | 0.226 | 2.893 |
|  | 1 month | 0.084 | 0.235 | 2.356 |
|  | 3 months | 0.084 | 0.239 | 2.472 |

Example 2: Pharmacokinetic Studies

Study A—Pharmacokinetic Profile in Mice

A single dose of bedaquiline was administered to the mouse orally and the plasma kinetics of bedaquiline itself (also referred to as "TMC207") and its main metabolite, N-monodesmethyl (also referred to as "M2"), were measured over a period of 168 hours. M2 seems to be an active metabolite and its formation, upon administration of bedaquiline (TMC207), is seen in at least the following species: mouse, rat/dog and human (its formation being the most in mouse and least in humans).

The results are as described in FIG. 1: "Plasma kinetics of TMC207 and M2 in mouse, after a single dose of 30 mg/kg"

It could be seen that:

TMC207 and M2 plasma kinetics are slow; the formation of M2 is also slow

M2 plasma exposure (AUC) is greater than the TMC207 exposure

M2 lung concentrations is a lot greater than TMC207 lung concentrations

After a period of 168 hours, the concentration of TMC207 in the plasma is about 0.01 µg/ml and of M2 is about 0.1 µg/ml As described in Example 1, the 200 mg/ml and 100 mg/ml micro- and nano-suspensions (Examples 1A, 1B, 1C and 1D) were tested on mice, where the mice either received:

a dose of 80 mg/kg (in which case the 100 mg/ml suspensions were used, i.e. Example 1C and 1D) or 160 mg/kg (in which case the 200 mg/ml suspensions were used, i.e. Example 1A and 1B)

were dosed intramuscularly (IM) or subcutaneously (SM)

Each of the formulations 1A, 1B, 1C and 1D were tested in a suspension API assay before administering into the mice, and it was determined that the API was in the range of 75-142% (an unusually broad range). However, in the mice, the plasma levels of bedaquiline and its metabolite could still be measured and assessed after administering such formulations.

Phase 1 of the Results—Up to 672 Hours

FIG. 2 "Plasma kinetics of TMC207 in mouse when administered IM or SC with 200 mg/ml formulations (specifically formulations of Examples 1A and 1B, i.e. the nano- and micro-suspension, respectively) at a dose of 160 mg/kg" (TMC207 is referred to the in the Figure as "UD")

FIG. 3 "Plasma kinetics of M2 in mouse when administered IM or SC with 200 mg/ml formulations (specifically formulations of Examples 1A and 1B, i.e. the nano- and micro-suspension, respectively) at a dose of 160 mg/kg" (M2 is referred to in the Figure as "met")

Generally, it can be seen that:

for the TMC207 concentrations, the $C_{max}$ ranges from between about 3000 ng/ml (the highest for the micro-suspension dosed IM) to about 100 ng/ml (the lowest being for the micro-suspension dosed SC)

at 672 hours, there was still a measureable concentration of TMC207 ranging from about 200 ng/ml (the highest for the micro-suspension dosed IM) to about 50 ng/ml (for lowest for the micro-suspension dosed SC)

for the M2 concentrations, the $C_{max}$ ranges from between about 3000 ng/ml (the highest for the micro-suspension dosed IM) to about 300 ng/ml (the lowest for the micro-suspension dosed SC)

at 672 hours, there was still a measureable concentration of M2 ranging from about 1000 ng/ml (the highest for the micro-suspension dosed IM) to about 200 ng/ml (the lowest for the micro-suspension dosed SC)

FIG. 4 "Plasma kinetics of TMC207 in mouse when administered IM or SC with 100 mg/ml formulations (specifically formulations of Examples 1C and 1D, i.e. the nano- and micro-suspension, respectively) at a dose of 80 mg/kg" (TMC207 is referred to the in the Figure as "UD")

FIG. 5 "Plasma kinetics of M2 in mouse when administered IM or SC with 100 mg/ml formulations (specifically formulations of Examples 1C and 1D, i.e. the nano- and micro-suspension, respectively) at a dose of 80 mg/kg" (M2 is referred to in the Figure as "met")

Generally, it can be seen that:

for the TMC207 concentrations, the $C_{max}$ ranges from between about 2000 ng/ml (the highest for the nano-suspension dosed IM) to about 400 ng/ml (the lowest being for the nano- and micro-suspension dosed SC)

at 672 hours, there was still a measureable concentration of TMC207 ranging from about 100 ng/ml (the highest for the micro-suspension dosed IM) to about 30 ng/ml (for lowest for the micro-suspension dosed SC)

for the M2 concentrations, the $C_{max}$ ranges from between about 2000 ng/ml (the highest for the nano-suspension dosed IM) to about 300 ng/ml (the lowest for the micro-suspension dosed SC)

at 672 hours, there was still a measureable concentration of M2 ranging from about 500 ng/ml (the highest for the micro-suspension dosed IM) to about 100 ng/ml (the lowest for the micro-suspension dosed SC)

Phase 2 of the Results—Up to 2184 Hours

The mice of these studies were further monitored up to 2184 hours, giving the following results:

for Formulation 1A, i.e. the nano-suspension of 200 mg/ml concentration, and dosed SC at 160 mg/kg (StDev=standard deviation) and IM at 160 mg/kg

| | Plasma concentration of bedaquiline (BDQ) or its metabolite (M2) | | | | | | | |
|---|---|---|---|---|---|---|---|---|
| | SC at 160 mg/kg | | | | IM at 160 mg/kg | | | |
| Time (h) | BDQ | StDev | M2 | StDev | BDQ | StDev | M2 | StDev |
| 1 | 493 | 305 | 59.3 | 49.6 | 1517 | 710 | 171 | 71 |
| 4 | 676 | 384 | 284 | 188 | 1588 | 662 | 708 | 332 |
| 7 | 728 | 269 | 484 | 312 | 1408 | 519 | 1063 | 456 |
| 24 | 726 | 53 | 956 | 289 | 1022 | 299 | 2071 | 828 |
| 168 | 239 | 28 | 1240 | 475 | 219 | 63 | 1399 | 557 |
| 336 | 138 | 66 | 759 | 282 | 99.0 | 33.2 | 597 | 301 |
| 504 | 122 | 53 | 503 | 178 | 66.1 | 26.1 | 418 | 209 |
| 672 | 109 | 22 | 383 | 136 | 79.0 | 34.8 | 405 | 211 |
| 840 | 100.8 | 42.5 | 196.0 | 76.5 | 69.6 | 58.5 | 119.2 | 60.3 |
| 1176 | 70.3 | 31.0 | 117.8 | 50.0 | 34.7 | 13.8 | 65.7 | 30.9 |
| 1512 | 58.5 | 20.1 | 91.2 | 42.5 | 23.4 | 8.4 | 40.3 | 18.1 |
| 1848 | 40.6 | 16.6 | 86.3 | 41.7 | 17.4 | 7.3 | 29.7 | 15.8 |
| 2184 | 35.2 | 21.4 | 65.1 | 36.6 | 14.5 | 6.7 | 27.3 | 13.2 |
| T max (h) | 4-24 | | 168 | | 1-4 | | 24 | |
| Cmax (ng/mL) | 862 | 202 | 1240 | 475 | 1723 | 764 | 2071 | 828 |
| t1/2 (h) | 910 | 442 | 1024 | 573 | 964 | 572 | 794 | 403 |
| AUClast (ng*h/mL) | 247783 | 54315 | 702286 | 173934 | 207109 | 69394 | 696089 | 302612 |

-continued

| | Plasma concentration of bedaquiline (BDQ) or its metabolite (M2) | | | | | | | |
|---|---|---|---|---|---|---|---|---|
| | SC at 160 mg/kg | | | | IM at 160 mg/kg | | | |
| Time (h) | BDQ | StDev | M2 | StDev | BDQ | StDev | M2 | StDev |
| AUCinf (ng*h/mL) | 301991 | 107533 | 815741 | 282889 | 231176 | 89366 | 728091 | 318248 | for Formulation 1C, i.e. the nano-suspension of 100 mg/ml concentration, and dosed SC at 80 mg/kg and IM at 80 mg/kg

| | Plasma concentration of bedaquiline (BDQ) or its metabolite (M2) | | | | | | | |
|---|---|---|---|---|---|---|---|---|
| | SC at 80 mg/kg | | | | IM at 80 mg/kg | | | |
| Time (h) | BDQ | StDev | M2 | StDev | BDQ | StDev | M2 | StDev |
| 1 | 261 | 66 | 22.0 | 3.5 | 1515 | 568 | 177 | 51 |
| 4 | 538 | 288 | 222 | 88 | 1572 | 470 | 684 | 239 |
| 7 | 480 | 281 | 342 | 108 | 1458 | 314 | 1049 | 256 |
| 24 | 205 | 109 | 545 | 185 | 1114 | 299 | 2186 | 834 |
| 168 | 65.6 | 30.9 | 298 | 130 | 186 | 46 | 1393 | 744 |
| 336 | 42.5 | 21.5 | 192 | 122 | 89.0 | 23.1 | 609 | 342 |
| 504 | 46.3 | 38.3 | 178 | 165 | 54.9 | 15.0 | 400 | 198 |
| 672 | 41.9 | 36.9 | 145 | 136 | 57.2 | 27.3 | 285 | 121 |
| 840 | 33.9 | 20.3 | 70.5 | 59.2 | 52.6 | 40.5 | 107 | 54 |
| 1176 | 25.4 | 15.9 | 47.2 | 37.5 | 28.2 | 17.8 | 50.4 | 29.9 |
| 1512 | 22.2 | 12.5 | 43.8 | 31.7 | 17.0 | 11.0 | 33.8 | 21.8 |
| 1848 | 14.1 | 7.3 | 28.8 | 18.8 | 12.6 | 9.1 | 23.2 | 17.4 |
| 2184 | 12.9 | 6.8 | 24.1 | 14.3 | 7.28 | | 18.3 | 14.2 |
| T max (h) | 4-7 | | 24 | | 1-7 | | 24 | |
| Cmax (ng/mL) | 557 | 265 | 545 | 185 | 1806 | 473 | 2186 | 834 |
| t1/2 (h) | 1051 | 390 | 796 | 147 | 581 | 159 | 650 | 122 |
| AUClast (ng*h/mL) | 84121 | 43933 | 238239 | 136814 | 186882 | 61016 | 669899 | 325833 |
| AUCinf (ng*h/mL) | 102985 | 47867 | 264292 | 149139 | 196358 | 68907 | 688601 | 344341 | for Formulation 1B, i.e. the micro-suspension of 200 mg/ml concentration, and dosed SC at 160 mg/kg (StDev=standard deviation) and IM at 160 mg/kg

| | Plasma concentration of bedaquiline (BDQ) or its metabolite (M2) | | | | | | | |
|---|---|---|---|---|---|---|---|---|
| | SC at 160 mg/kg | | | | IM at 160 mg/kg | | | |
| Time (h) | BDQ | StDev | M2 | StDev | BDQ | StDev | M2 | StDev |
| 1 | 71.1 | 15.1 | 6.53 | 2.02 | 1737 | 1752 | 206 | 247 |
| 4 | 101 | 7 | 37.5 | 7.1 | 2258 | 1229 | 908 | 734 |
| 7 | 102 | 12 | 55.3 | 17.7 | 1764 | 1103 | 1474 | 795 |
| 24 | 130 | 19 | 186 | 36 | 1306 | 407 | 2926 | 1143 |
| 168 | 78.7 | 5.3 | 276 | 61 | 391 | 137 | 2643 | 1087 |
| 336 | 53.8 | 3.5 | 226 | 45 | 293 | 131 | 1693 | 798 |
| 504 | 51.1 | 8.3 | 196 | 37 | 222 | 101 | 1526 | 773 |
| 672 | 67.4 | 12.8 | 266 | 52 | 231 | 115 | 1202 | 680 |
| 840 | 65.7 | 28.9 | 114.3 | 36.6 | 163.5 | 74.1 | 387.8 | 198.0 |
| 1176 | 55.1 | 36.2 | 104.6 | 51.3 | 121.9 | 48.7 | 255.0 | 137.4 |
| 1512 | 38.2 | 13.6 | 95.6 | 34.4 | 94.0 | 60.7 | 165.2 | 91.2 |
| 1848 | 36.9 | 11.0 | 66.7 | 22.8 | 65.6 | 23.3 | 146.4 | 80.8 |
| 2184 | 30.7 | 10.4 | 60.9 | 21.9 | 51.5 | 26.1 | 112 | 62 |
| T max (h) | 24 | | 168-672 | | 1-4 | | 24-168 | |
| Cmax (ng/mL) | 130 | 19 | 309 | 30 | 2364 | 1447 | 3002 | 1139 |
| t1/2 (h) | 1545 | 253 | 1294 | 383 | 719 | 70 | 848 | 273 |
| AUClast (ng*h/mL) | 117569 | 30034 | 300334 | 63219 | 447361 | 174979 | 1689422 | 755169 |

-continued

| | Plasma concentration of bedaquiline (BDQ) or its metabolite (M2) | | | | | | | |
|---|---|---|---|---|---|---|---|---|
| | SC at 160 mg/kg | | | | IM at 160 mg/kg | | | |
| Time (h) | BDQ | StDev | M2 | StDev | BDQ | StDev | M2 | StDev |
| AUCinf (ng*h/mL) | 188153 | 60663 | 412456 | 107222 | 500850 | 201928 | 1823672 | 836740 | for Formulation 1D, i.e. the micro-suspension of 100 mg/ml concentration, and dosed SC at 80 mg/kg (StDev=standard deviation) and IM at 80 mg/kg

| | Plasma concentration of bedaquiline (BDQ) or its metabolite (M2) | | | | | | | |
|---|---|---|---|---|---|---|---|---|
| | SC at 80 mg/kg | | | | IM at 80 mg/kg | | | |
| Time (h) | BDQ | StDev | M2 | StDev | BDQ | StDev | M2 | StDev |
| 1 | 133 | 114 | | 6.70 | 463 | 186 | 29.7 | 12.1 |
| 4 | 415 | 533 | 130 | 175 | 873 | 221 | 264 | 41 |
| 7 | 350 | 412 | 232 | 310 | 850 | 200 | 459 | 60 |
| 24 | 162 | 47 | 360 | 364 | 709 | 228 | 1101 | 341 |
| 168 | 53.2 | 18.3 | 226 | 112 | 209 | 44 | 1050 | 405 |
| 336 | 28.7 | 6.8 | 107 | 35 | 112 | 12 | 547 | 150 |
| 504 | 28.2 | 0.8 | 109 | 27 | 71.8 | 17.5 | 398 | 121 |
| 672 | 28.6 | 5.8 | 105 | 33 | 87.0 | 17.0 | 444 | 127 |
| 840 | 25.9 | 6.8 | 56.3 | 22.9 | 70.9 | 19.6 | 130 | 36 |
| 1176 | 25.3 | 4.5 | 42.9 | 15.8 | 41.5 | 8.4 | 91.2 | 27.4 |
| 1512 | 20.2 | 6.9 | 42.1 | 16.4 | 31.1 | 9.5 | 68.8 | 26.8 |
| 1848 | 19.6 | 8.0 | 31.5 | 14.7 | 24.0 | 7.0 | 43.7 | 15.2 |
| 2184 | 15.2 | 5.4 | 32.7 | 16.1 | 26.3 | 14.2 | 42.2 | 16.7 |
| T max (h) | 4-24 | | 24-168 | | 4-7 | | 24-168 | |
| Cmax (ng/mL) | 433 | 517 | 383 | 348 | 925 | 192 | 1139 | 366 |
| t1/2 (h) | 1423 | 535 | 1082 | 437 | 916 | 337 | 734 | 322 |
| AUClast (ng*h/mL) | 69275 | 7996 | 175236 | 48413 | 192325 | 36480 | 586546 | 165428 |
| AUCinf (ng*h/mL) | 103115 | 29066 | 226669 | 50867 | 225966 | 51489 | 632846 | 193499 |

Study B—Pharmacokinetic Profile in Rats and Beagle Dogs

Formulations of concentrations 200 mg/mL were used in this study, both the nano-suspension (Formulation 1A) and the micro-suspension (Formulation 1B), as depicted above in Example 1 (i.e. using, in addition to the 200 mg/ml concentration of micro- and nano-particles (of the active bedaquiline), TPGS (4:1 bedaquiline:TPGS) and 50 mg/ml Mannitol in WFI (water for injection)).

These studies demonstrate that formulations described in Example 1 (specifically the nano- and micro-formulations 1A and 1B) results in stable plasma levels over a prolonged period of time in male rats and male beagle dogs, when administered subcutaneously (SC) and intramuscularly (IM).

Male Rats

The first experiment was performed on male rats, where each relevant 200 mg/ml nano-suspension and micro-suspension referred to above were administered subcutaneously (SC) and intramuscularly (IM) at a concentration of 40 mg/kg (0.2 mL/kg). An interim analysis was performed at 3 months and the results were followed-up at 6 months. Twelve rats were used in the study. Six rats were dosed intramuscularly (IM), three of those rats with the 200 mg/ml nano-suspension (see Example 1, Formulation 1A above) and the other three with the 200 mg/ml micro-suspension (see Example 1, Formulation 1B above). Six rats were dosed subcutaneously (SC), three of those rats with the 200 mg/ml nano-suspension (see Formulation 1A above) and the other three with the 200 mg/ml micro-suspension (see Formulation 1B above).

Phase 1 of the Results—Up to 2200 Hours

FIG. 6 "Plasma kinetics of TMC207 in male rats when administered IM or SC with 200 mg/ml micro-formulation (see Example 1, Formulation 1B i.e. the micro-suspension) at a dose of 40 mg/kg" and "Plasma kinetics of TMC207 in male rats when administered IM or SC with 200 mg/ml nano-formulation (see Example 1, Formulation 1A, i.e. the nano-suspension) at a dose of 40 mg/kg"

The following parameters were calculated for TMC207 (see FIG. 6):

| | Microsuspension (Form IB) SC | Microsuspension (Form IB) IM | Nanosuspension (Form 1A) SC | Nanosuspension (Form 1A) IM |
|---|---|---|---|---|
| n | 3 | 3 | 3 | 3 |
| $C_{max}$ (ng/ml) | 68.1 ± 17.6 | 215 ± 66.7 | 337 ± 57.0 | 505 ± 96.6 |

-continued

| n | Microsuspension (Form IB) SC 3 | Microsuspension (Form IB) IM 3 | Nanosuspension (Form 1A) SC 3 | Nanosuspension (Form 1A) IM 3 |
|---|---|---|---|---|
| $T_{max}{}^a$ (h) | 24 (24.00-24.00) | 18 (7.00-24.00) | 24 (24.00-24.00) | 16 (1.00-24.00) |
| $T_{last}{}^a$ = around 3 mths (h) | 2184 (2184-2184) | 2184 (2184-2184) | 2184 (2184-2184) | 2184 (2184-2184) |
| $AUC_{0-2184h}$ (3 mths) (ng·h/ml) | 34700 ± 1770 | 91500 ± 13200 | 75400 ± 5070 | 77900 ± 8930 | where applicable mean values are given (with min→max in parentheses)
Generally, it can be seen that:
  after microsuspension administration, higher (2.6 fold) AUC after IM versus SC. After nanosuspension administration, similar AUC after SC or IM
  in terms of bioavailability (comparison with IV 5 mg/kg), for the lowest (microsuspension SC)=56%, for the 3 other >100%
  M2, which is not specified on the graphs in FIG. 6, has the same profiles as TMC207 except that $t_{max}$ is later, AUC of M2 is 1.5 to 2 fold lower than TMC207; in general this ratio is comparable to PO route
A comparison was also performed with oral (PO) administration in rats, which can also be considered a 13 week toxicity study, where the following result was observed:
  The exposures ($C_{max}$ and AUC) at 3 months after single IM or SC for both formulations are much lower than the total exposure after PO administration at the top dose of 13 week study: IM/SC 34500-91500 ng·h/mL versus PO a total exposure=2 385 383 ng·h/mL during the same period of time (3 months)
  see above regarding M2

Male Beagle Dogs

The second experiment was performed on male beagle dogs, where each relevant 200 mg/ml nano-suspension and micro-suspension referred to above were administered subcutaneously (SC) and intramuscularly (IM) at a concentration of 40 mg/kg (0.2 mL/kg). An interim analysis was performed at 3 months and the results were followed-up at 6 months. Twelve (12) healthy male beagle dogs with body weights ranging from 8 to 16 kg at the start of the study, were used. Each dog was identified by an ear tattoo number. Six dogs were dosed intramuscularly (IM) in the left and right m. biceps femoris, three of those dogs with the 200 mg/ml nano-suspension (see Example 1, Formulation 1A above) and the other three with the 200 mg/ml micro-suspension (see Example 1, Formulation 1B). Six dogs were dosed subcutaneously (SC) in the left and right thoracal region, three of those dogs with the 200 mg/ml nano-suspension (see Formulation 1A above) and the other three with the 200 mg/ml micro-suspension (see Formulation 1B above).

Blood samples of 3 ml were taken from the left jugular vein from all dogs on day 0 at 0 h (predose), 20 min, 1 h, 3 h, 8 h and 24 h post-dose and further on days 2, 3, 6, 8, 10, 13, 16, 20, 23, 27, 29, 36, 43, 50, 57, 64, 71, 78, 85 and 92 at approximately 8 AM. Blood samples were placed on EDTA, EDTA Vacuette Greiner, Cat. No. 454086, Greiner Labortechnik N.V.). Within 2 h of blood sampling, samples were centrifuged at room temperature at about 1900×g for 10 minutes to allow plasma separation. Plasma was immediately transferred into a second tube and stored in the freezer within 2 hours after the start of centrifugation. Plasma samples were analysed individually for TMC207, and for its metabolite M2, by means of a validated LC-MS/MS-method.

FIG. 7 "Plasma kinetics of TMC207 in male beagle dogs when administered IM or SC with 200 mg/ml micro-formulation (see Example 1, Formulation 1B) at a dose of 40 mg/kg" and "Plasma kinetics of TMC207 in male beagle dogs when administered IM or SC with 200 mg/ml nano-formulation (see Example 1, Formulation 1A) at a dose of 40 mg/kg"

The following parameters were calculated for TMC207 (see FIG. 7):

| n | Microsuspension (Form 1B) SC 3 | Microsuspension (Form 1B) IM 3 | Nanosuspension (Form 1A) SC 3 | Nanosuspension (Form 1B) IM 3 |
|---|---|---|---|---|
| $C_{max}$ (ng/ml) | 219 ± 237 | 822 ± 211 | 692 ± 217 | 4150 ± 1290 |
| $T_{max}{}^a$ (h) | 620 (168.00-840.00) | 3.0 (1.00-7.00) | 168 (168.00-168.00) | 2.0 (1.00-4.00) |
| $T_{last}{}^a$ = around 3 mths (h) | 2184 (2184-2184) | 2184 (2184-2184) | 2184 (2184-2184) | 2184 (2184-2184) |
| $AUC_{last}$ (ng·h/ml) | 268000 ± 250000 | 519000 ± 64300 | 483000 ± 65300 | 549000 ± 26200 | where applicable mean values are given (with min→max in parentheses)
Generally, it can be seen that:
  after microsuspension administration, higher (2 fold) AUC after IM versus SC
  after nanosuspension administration, similar AUC after SC or IM
  in terms of $C_{max}$ higher after IM versus SC for both formulation
  in terms of bioavailability (comparison with IV 1 mg/kg) >100%

M2 has the same profiles as TMC207 except that $t_{max}$ is later, AUC is 3 to 4 fold lower than TMC207; in general this ratio is comparable to PO route A comparison was also performed with oral (PO) administration in rats, which can be considered as a 13 week toxicity study, where the following result was observed:

The highest $C_{max}$ after IM nanosuspension similar to the $C_{max}$ after PO at 18 mg/kg; in terms of exposure much higher total exposure after PO versus after IM/SC: IM/SC 268000-549000 ng·h/mL versus PO a total exposure=13 988 520 ng·h/mL for the same period See above for M2

Based on the 3-month interim results, we have the following conclusions:

After IM/SC nanosuspension/microsuspesion:
In rats, AUC: IM micro>SCnano~=IM nano (more rapid decline)>SC micro
In dogs, AUC: IM micro>SCnano~=IM nano>SC micro (similar decline for the 4 profiles)

At 40 mg/kg after IM/SC nanosuspension/microsuspension, $C_{max}$ and AUC of TMC207/M2 are covered by oral tox studies in both species except for the $C_{max}$ of TMC207 in dogs after IM nanosuspension which is similar between PO and IM Phase 2 of the Results—Up to 4400 Hours In all cases the plasma concentration of BDQ or M2 is calculated as the mean of the three animals (rats or dogs) in the relevant study.

Study in rats: for Formulation 1B, i.e. the micro-suspension of 200 mg/ml concentration, and dosed SC at 40 mg/kg (StDev=standard deviation) and IM at 40 mg/kg

| | Plasma concentration of bedaquiline (BDQ) or its metabolite (M2) | | | | | | | |
|---|---|---|---|---|---|---|---|---|
| | SC at 40 mg/kg | | | | IM at 40 mg/kg | | | |
| Time (h) | BDQ | StDev | M2 | StDev | BDQ | StDev | M2 | StDev |
| 1 | 22.1 | 5.36 | 0.589 | NC | 139 | 33.2 | 5.11 | 2.24 |
| 4 | 36.9 | 7.42 | 6.62 | 1.69 | 172 | 47.2 | 18.8 | 5.98 |
| 7 | 40.7 | 6.27 | 8.59 | 1.46 | 185 | 24.2 | 28.7 | 7.57 |
| 24 | 68.1 | 17.6 | 24.0 | 1.14 | 212 | 70.6 | 77.3 | 23.5 |
| 168 | 16.5 | 4.84 | 9.03 | 1.81 | 98.0 | 19.1 | 91.5 | 33.1 |
| 336 | 18.1 | 3.30 | 9.28 | 2.10 | 69.7 | 10.2 | 54.9 | 16.8 |
| 504 | 22.8 | 3.96 | 9.68 | 2.85 | 52.2 | 4.05 | 37.9 | 16.5 |
| 672 | 14.7 | 0.964 | 7.32 | 1.34 | 42.6 | 6.85 | 29.5 | 14.8 |
| 840 | 15.1 | 1.74 | 7.40 | 2.46 | 33.6 | 6.39 | 22.3 | 10.6 |
| 1008 | 14.7 | 3.47 | 6.82 | 2.06 | 28.5 | 6.24 | 20.2 | 11.2 |
| 1176 | 13.2 | 2.99 | 5.96 | 1.76 | 24.1 | 7.04 | 16.6 | 9.37 |
| 1344 | 12.4 | 2.34 | 6.10 | 1.79 | 20.7 | 3.07 | 14.1 | 8.88 |
| 1512 | 12.0 | 0.917 | 5.81 | 1.81 | 19.7 | 5.98 | 13.4 | 7.16 |
| 1680 | 12.3 | 1.95 | 5.42 | 2.01 | 18.4 | 3.30 | 11.5 | 5.77 |
| 1848 | 10.6 | 0.83 | 5.18 | 1.51 | 14.3 | 1.35 | 11.4 | 6.39 |
| 2016 | 9.83 | 2.06 | 4.30 | 2.03 | 14.9 | 1.75 | 9.86 | 3.75 |
| 2184 | 10.2 | 2.42 | 4.55 | 1.36 | 12.6 | 0.755 | 8.87 | 3.37 |
| 2520 | 9.45 | 2.16 | 5.54 | 1.82 | 11.6 | 2.06 | 9.27 | 3.53 |
| 2856 | 8.26 | 0.737 | 4.78 | 1.61 | 10.5 | 2.65 | 7.49 | 3.02 |
| 3192 | 6.82 | 1.38 | 4.04 | 1.02 | 8.67 | 2.71 | 6.28 | 2.52 |
| 3528 | 6.83 | 2.27 | 4.02 | 1.05 | 6.92 | 2.09 | 5.68 | 2.79 |
| 3864 | 6.69 | 0.794 | 3.95 | 0.866 | 5.90 | 2.21 | 5.00 | 2.53 |
| 4200 | 6.41 | 1.72 | 3.49 | 0.987 | 4.41 | 2.04 | 3.74 | 2.03 |
| ≈ CV % | 8-29 | | NC-47 | | 6-46 | | 26-63 | |
| T max (h) | 24 | | 24 | | 18 | | 120 | 83 |
| Cmax (ng/mL) | 68.1 | 17.6 | 24.0 | 1.14 | 215 | 66.7 | 94.2 | 33.3 |
| T last (h) | 4200 | | 4200 | | 4200 | | 4200 | |
| AUClast (ng*h/mL) | 50200 | 4240 | 24800 | 5520 | 109000 | 12300 | 75200 | 28700 |
| $AUC_{0-2856}$ (ng*h/mL) | 41000 | 2880 | 19300 | 4150 | 99200 | 13200 | 67600 | 26100 |
| AUCinf (ng*h/mL) | NC | | NC | | 121000 | 11400 | 85500 | 28800 |

Study in Rats: for Formulation 1A, i.e. the nano-suspension of 200 mg/ml concentration, and dosed SC at 40 mg/kg (StDev=standard deviation) and IM at 40 mg/kg (in this case, small sample size applied to calculation of summary variable)

| | Plasma concentration of bedaquiline (BDQ) or its metabolite (M2) | | | | | | | |
|---|---|---|---|---|---|---|---|---|
| | SC at 40 mg/kg | | | | IM at 40 mg/kg | | | |
| Time (h) | BDQ | StDev | M2 | StDev | BDQ | StDev | M2 | StDev |
| 1 | 42.1 | 11.4 | BOL[a] | NC | 329 | 256 | 12.0 | 5.77 |
| 4 | 81.5 | 17.0 | 11.7 | 3.50 | 365 | 176 | 39.5 | 16.7 |

-continued

| | Plasma concentration of bedaquiline (BDQ) or its metabolite (M2) | | | | | | | |
|---|---|---|---|---|---|---|---|---|
| | SC at 40 mg/kg | | | | IM at 40 mg/kg | | | |
| Time (h) | BDQ | StDev | M2 | StDev | BDQ | StDev | M2 | StDev |
| 7 | 98.7 | 25.2 | 20.3 | 4.15 | 385 | 124 | 68.6 | 30.4 |
| 24 | 337 | 57.0 | 127 | 20.8 | 436 | 41.2 | 217 | 36.3 |
| 168 | 92.4 | 33.6 | 100 | 17.7 | 94.9 | 25.1 | 89.9 | 21.8 |
| 336 | 62.7 | 5.61 | 62.9 | 25.3 | 53.0 | 13.0 | 48.6 | 21.2 |
| 504 | 42.1 | 6.21 | 45.8 | 30.7 | 36.2 | 7.49 | 26.6 | 12.0 |
| 672 | 28.4 | 1.04 | 32.4 | 22.5 | 22.4 | 3.35 | 15.8 | 5.31 |
| 840 | 20.8 | 3.67 | 21.1 | 13.4 | 25.9 | 2.48 | 11.1 | 2.50 |
| 1008 | 16.5 | 4.56 | 16.2 | 12.0 | 12.0 | 1.55 | 8.13 | 1.82 |
| 1176 | 12.7 | 4.58 | 12.7 | 10.0 | 9.05 | 1.23 | 5.74 | 1.07 |
| 1344 | 12.0 | 7.04 | 10.1 | 9.35 | 7.33 | 0.739 | 4.20 | 1.18 |
| 1512 | 7.02 | 2.77 | 7.61 | 6.32 | 4.69 | 0.384 | 3.05 | 0.640 |
| 1680 | 6.05 | 2.79 | 6.02 | NC | 4.57 | 0.378 | 2.63 | 0.242 |
| 1848 | 4.95 | 2.56 | 5.35 | 5.22 | 4.05 | 0.192 | 1.56 | NC |
| 2016 | 4.36 | 2.12 | 4.08 | NC | 3.21 | 0.646 | 1.92 | 0.246 |
| 2184 | 3.77 | 1.94 | 3.49 | NC | 2.50 | 0.0231 | 1.80 | 0.102 |
| 2520 | 2.72 | 1.67 | 2.97 | 2.62 | 2.27 | 0.437 | 1.45 | 0.121 |
| 2856 | 2.51 | 0.880 | 2.50 | 2.16 | 1.56 | 0.335 | 0.926 | 0.0759 |
| 3192 | 1.51 | 0.892 | 2.14 | NC | 1.26 | 0.275 | 0.841 | 0.0826 |
| 3528 | 1.50 | NC | 1.28 | NC | 1.37 | NC | BOL[a] | NC |
| 3864 | 0.887 | NC | BOL[a] | NC | BOL[a] | NC | BOL[a] | NC |
| 4200 | 0.753 | NC | BOL[a] | NC | BOL[a] | NC | BOL[a] | NC |
| ≈ CV % | NC-61 | | NC-90 | | 1-78 | | NC-48 | |
| T max (h) | 24 | | 24 | | 16 | | 24 | |
| Cmax (ng/mL) | 337 | 57.0 | 127 | 20.8 | 505 | 96.6 | 217 | 36.3 |
| T last (h) | 3900 | 580 | 3500 | 670 | 3500 | 340 | 3300 | 190 |
| AUClast (ng*h/mL) | 79100 | 3100 | 67200 | 33600 | 80400 | 8260 | 53400 | 10700 |
| AUC$_{0-2856}$ (ng*h/mL) | 77300 | 4240 | 65400 | 31200 | 79400 | 8800 | 53000 | 10700 |
| AUCinf (ng*h/mL) | 80100 | 2890 | 68600 | 34500 | 81200 | 8230 | 54000 | 10700 |

NC = not calculated
BOL[a] = below limit of quantification (0.75 ng/mL or 1.5 ng/mL)

Study in Dogs: for Formulation 1B, i.e. the micro-suspension of 200 mg/ml concentration, and dosed SC at 40 mg/kg (StDev=standard deviation) and IM at 40 mg/kg.

| | Plasma concentration of bedaquiline (BDQ) or its metabolite (M2) | | | | | | | |
|---|---|---|---|---|---|---|---|---|
| | SC at 40 mg/kg | | | | IM at 40 mg/kg | | | |
| Time (h) | BDQ | StDev | M2 | StDev | BDQ | StDev | M2 | StDev |
| 1 | 1.55 | 0.0794 | BOL[a] | NC | 765 | 136 | BOL[a] | NC |
| 4 | 5.43 | 1.48 | BOL[a] | NC | 703 | 292 | 14.9 | 5.87 |
| 7 | 8.80 | 2.48 | BOL[a] | NC | 735 | 274 | 21.2 | 8.72 |
| 24 | 21.9 | 13.0 | BOL[a] | NC | 349 | 28.3 | 27.7 | 9.76 |
| 168 | 192 | 261 | 32.9 | 40.1 | 351 | 65.6 | 69.8 | 11.6 |
| 336 | 160 | 173 | 47.1 | 46.9 | 355 | 30.2 | 94.2 | 7.02 |
| 504 | 149 | 151 | 50.4 | 51.5 | 338 | 30.0 | 93.8 | 13.2 |
| 672 | 123 | 109 | 46.2 | 43.1 | 284 | 37.8 | 90.6 | 16.9 |
| 840 | 161 | 138 | 53.1 | 48.2 | 315 | 30.1 | 96.2 | 3.24 |
| 1008 | 125 | 104 | 50.1 | 40.1 | 227 | 25.2 | 80.7 | 4.11 |
| 1176 | 116 | 96.4 | 42.8 | 34.9 | 187 | 45.1 | 60.8 | 13.0 |
| 1344 | 110 | 96.2 | 40.4 | 31.9 | 172 | 38.7 | 52.8 | 11.1 |
| 1512 | 108 | 93.5 | 41.0 | 35.7 | 171 | 34.4 | 62.1 | 14.2 |
| 1680 | 136 | 107 | 39.7 | 31.9 | 183 | 37.6 | 51.8 | 6.85 |
| 1848 | 93.0 | 75.4 | 37.4 | 30.4 | 135 | 43.4 | 46.9 | 9.40 |
| 2016 | 89.5 | 71.4 | 35.9 | 26.0 | 121 | 31.1 | 41.2 | 7.86 |
| 2184 | 82.0 | 59.8 | 28.6 | 23.4 | 108 | 28.4 | 37.1 | 9.31 |
| 2520 | 83.1 | 58.8 | 29.8 | 24.3 | 88.0 | 28.4 | 29.2 | 7.60 |
| 2856 | 75.3 | 53.5 | 28.8 | 23.2 | 74.3 | 23.5 | 26.4 | 5.30 |
| 3192 | 60.3 | 36.1 | 23.8 | 15.4 | 58.7 | 17.6 | 22.1 | 5.17 |
| 3528 | 59.1 | 34.3 | 20.3 | 13.4 | 54.0 | 17.2 | 18.9 | 6.60 |
| 3864 | 52.8 | 26.0 | 20.1 | 11.0 | 45.4 | 15.8 | 16.4 | 5.17 |
| 4200 | 51.7 | 30.2 | 20.4 | 13.2 | 40.9 | 14.6 | 15.6 | 4.63 |

-continued

| | Plasma concentration of bedaquiline (BDQ) or its metabolite (M2) | | | | | | | |
|---|---|---|---|---|---|---|---|---|
| | SC at 40 mg/kg | | | | IM at 40 mg/kg | | | |
| Time (h) | BDQ | StDev | M2 | StDev | BDQ | StDev | M2 | StDev |
| ≈ CV % | 5-136 | | NC-122 | | 8-42 | | 3-41 | |
| T max (h) | 620 | 390 | 780 | 260 | 3.0 | | 620 | 260 |
| Cmax (ng/mL) | 219 | 237 | 55.3 | 47.7 | 822 | 211 | 103 | 6.58 |
| T last (h) | 4200 | | 4200 | | 4200 | | 4200 | |
| AUClast (ng*h/mL) | 402000 | 335000 | 138000 | 114000 | 652000 | 105000 | 193000 | 27900 |
| AUCinf (ng*h/mL) | NC | | NC | NC | 690000 | NC | NC | NC |

NC = not calculated
BOL$^a$ = below limit of quantification (3.75 ng/mL)

Study in Dogs: for Formulation 1A, i.e. the nano-suspension of 200 mg/ml concentration, and dosed SC at 40 mg/kg (StDev=standard deviation) and IM at 40 mg/kg (in this case, small sample size applied to calculation of summary variable)

| | Plasma concentration of bedaquiline (BDQ) or its metabolite (M2) | | | | | | | |
|---|---|---|---|---|---|---|---|---|
| | SC at 40 mg/kg | | | | IM at 40 mg/kg | | | |
| Time (h) | BDQ | StDev | M2 | StDev | BDQ | StDev | M2 | StDev |
| 1 | 274 | 466 | BOL$^a$ | NC | 4000 | 1510 | 11.1 | 1.35 |
| 4 | 194 | 197 | BOL$^a$ | NC | 3570 | 620 | 41.7 | 7.25 |
| 7 | 157 | 134 | 4.94 | NC | 2690 | 842 | 51.5 | 10.6 |
| 24 | 167 | 52.6 | 8.68 | 6.84 | 742 | 82.3 | 62.6 | 17.2 |
| 168 | 692 | 217 | 127 | 54.6 | 568 | 142 | 108 | 27.1 |
| 336 | 386 | 55.4 | 132 | 29.0 | 412 | 19.2 | 112 | 24.4 |
| 504 | 318 | 76.8 | 110 | 7.77 | 321 | 13.1 | 98.4 | 21.0 |
| 672 | 244 | 28.4 | 93.8 | 14.9 | 240 | 29.6 | 84.1 | 25.0 |
| 840 | 255 | 29.7 | 93.0 | 5.84 | 254 | 12.7 | 89.4 | 24.5 |
| 1008 | 197 | 40.6 | 74.8 | 2.20 | 172 | 23.4 | 63.7 | 16.2 |
| 1176 | 158 | 21.4 | 59.5 | 4.92 | 149 | 10.0 | 58.7 | 13.0 |
| 1344 | 133 | 19.5 | 47.3 | 2.10 | 139 | 13.2 | 47.1 | 12.8 |
| 1512 | 124 | 25.4 | 46.4 | 5.82 | 120 | 8.62 | 41.6 | 10.6 |
| 1680 | 136 | 24.0 | 43.6 | 3.40 | 126 | 17.0 | 44.5 | 11.7 |
| 1848 | 89.6 | 23.8 | 33.8 | 3.53 | 95.2 | 2.14 | 32.7 | 4.60 |
| 2016 | 84.5 | 18.8 | 31.6 | 3.04 | 89.9 | 16.7 | 31.7 | 7.72 |
| 2184 | 80.5 | 25.4 | 27.9 | 3.52 | 78.4 | 5.66 | 24.5 | 6.07 |
| 2520 | 59.7 | 14.8 | 21.1 | 2.04 | 57.4 | 4.47 | 19.4 | 3.07 |
| 2856 | 53.9 | 18.0 | 19.6 | 4.25 | 54.8 | 3.04 | 18.7 | 2.77 |
| 3192 | 45.2 | 16.7 | 16.4 | 4.19 | 42.9 | 4.32 | 14.5 | 2.80 |
| 3528 | 40.0 | 12.3 | 14.9 | 3.55 | 36.1 | 1.40 | 12.4 | 2.06 |
| 3864 | 34.5 | 13.1 | 12.8 | 3.20 | 32.3 | 2.42 | 11.5 | 1.82 |
| 4200 | 31.1 | 14.1 | 12.1 | 4.02 | 25.4 | 1.37 | 9.49 | 1.42 |
| ≈ CV % | 12-170 | | NC-79 | | 2-38 | | 12-30 | |
| T max (h) | 168 | | 280 | 97 | 3 | 2.0 | 280 | 97 |
| Cmax (ng/mL) | 692 | 217 | 140 | 42.8 | 4150 | 1290 | 121 | 21.7 |
| T last (h) | 4200 | | 4200 | | 4200 | | 4200 | |
| AUClast (ng*h/mL) | 580000 | 82500 | 186000 | 8740 | 641000 | 27700 | 174000 | 32900 |
| AUCinf (ng*h/mL) | NC | NC | 215000 | NC | 677000 | 24800 | 193000 | 32200 |

NC = not calculated
BOL$^a$ = below limit of quantification (0.75 ng/mL)

Example 3

Evaluation of an Injectable, Long-Acting Bedaquiline Formulation in the Paucibacillary Mouse Model of Latent Tuberculosis Infection The objective of this study was to use the paucibacillary mouse model of latent tuberculosis infection (LTBI) to compare the bactericidal activity of a long-acting bedaquiline ($B_{LA}$) formulation administered every 4 weeks for a total of 1, 2, or 3 doses to the activity of daily (5 days per week) oral dosing of B at the standard 25 mg/kg dose or lower doses matching to total drug doses administered as $B_{LA}$. The original study scheme is presented in Table 1. The $B_{LA}$ used for this study is that described above in Example 1B, i.e. the microsuspension at a concentration of 200 mg/ml). The primary outcome was the decline in *Mycobacterium tuberculosis* lung CFU counts during treatment.

TABLE 1

Original study scheme to evaluate the bactericidal activity of $B_{LA}$ in a mouse model of paucibacillary LTBI.

| LTBI treatment regimen* | BCG immunization Week 12 | M.tb. challenge Week 6 | Treatment initiation Day 0 | Number of mice sacrificed for lung CFU counts at the following time points: During treatment | | | Total mice | Total dose B over 12 weeks (mg/kg) |
|---|---|---|---|---|---|---|---|---|
| | | | | Week 4 | Week 8 | Week 12 | | |
| Untreated | 5 | 5 | 5 | 5 | 5 | 5 | 30 | na |
| $R_{10}$ (5/7) | | | | 5 | 5 | 5 | 15 | na |
| $P_{15}H_{50}$ (1/7) | | | | 5 | 5 | 5 | 15 | na |
| $B_{25}$ (5/7) | | | | 5 | 5 | 5 | 15 | 1500 |
| $B_8$ (5/7) | | | | 5 | 5 | 5 | 15 | 480 |
| $B_{5.33}$ (5/7) | | | | 5 | 5 | 5 | 15 | 320 |
| $B_{2.67}$ (5/7) | | | | 5 | 5 | | 15 | 160 |
| $B_{LA-160}$ (1/28) × 3 | | | | | | 5 | 5 | 480 |
| $B_{LA-160}$ (1/28) × 2 | | | | | 5 | 5 | 10 | 320 |
| $B_{LA-160}$ (1/28) × 1 | | | | 5 | 5 | 5 | 15 | 160 |
| Total mice | 5 | 5 | 5 | 40 | 45 | 50 | 150 | |

*R, rifampin; P, rifapentine; H, isoniazid; B, bedaquiline; $B_{LA}$, long-acting bedaquiline formulation.
All drug doses in mg/kg indicated by subscript.
Fractions in parentheses indicate dosing frequency, in days.
$B_{LA}$ is administered by intramuscular injection; all other drugs are administered by gavage.
na, not applicable.

Justification of the Regimens

Untreated mice were used to determine the level and stability of the paucibacillary infection.

$R_{10}$ (5/7) is an alternative regimen for treatment of LTBI in the US and Canada, administered for 4 months. It was used here as a control to qualify the model.

$P_{15}H_{50}$ (1/7) is an alternative regimen for treatment of LTBI in the US, administered once weekly for 3 months (12 doses). It proved at least as efficacious as 9 months of isoniazid. It is the most intermittent of currently recommended regimens and serves as a second control.

$B_{25}$ (5/7) is daily B at the human equivalent dose previously studied in the paucibacillary model. It provides a total dose of 500 mg/kg every 28 days.

$B_8$ (5/7) is daily B at a dose that is reduced to provide the same total dose (480 mg/kg) as the $B_{LA}$ formulation dose (i.e., 160 mg/kg) administered every 28 days×3 doses.

$B_{5.33}$ (5/7) is daily B at a dose that is reduced to provide the same total dose (320 mg/kg) as the $B_{LA}$ formulation dose (i.e., 160 mg/kg) administered every 28 days×2 doses.

$B_{2.67}$ (5/7) is daily B at a dose that is reduced to provide the same total dose (160 mg/kg) as the $B_{LA}$ formulation dose (i.e., 160 mg/kg) administered once.

$B_{LA-160}$ (1/28)×3 is the $B_{LA}$ formulation administered as 160 mg/kg every 28 days for a total of 3 doses. Thus, the total B dose will match that of the $B_8$ (5/7) group at each 28-day interval.

$B_{LA-160}$ (1/28)×2 is the $B_{LA}$ formulation administered as 160 mg/kg every 28 days for a total of 2 doses, beginning on Day 0. Thus, the total B dose administered by Week 12 (320 mg/kg) will be the same as that of the $B_{5.33}$ (5/7) group.

$B_{LA-160}$ (1/28)×1 is the $B_{LA}$ formulation administered as 160 mg/kg just once on Day 0. Thus, the total B dose administered by Week 12 (160 mg/kg) will be the same as that in the $B_{2.67}$ (5/7) group.

Final Results

All CFU count data are finalized and presented below in Table 2. Due to delays in finalizing institutional agreements and obtaining the $B_{LA}$ supply, treatment was not initiated until approximately 13 weeks after the M. tuberculosis challenge infection, and the time line in Table 2 has been adjusted accordingly. For comparison between different treatment groups, statistical significance was assessed using one-way ANOVA adjusted with Bonferroni's multiple comparisons test.

TABLE 2

Final M. tuberculosis lung CFU count data.

| LTBI treatment regimen* | Mean (SD) $\log_{10}$ M. tuberculosis CFU/lung at the following time points: | | | | | | Total dose B over 12 weeks (mg/kg) |
|---|---|---|---|---|---|---|---|
| | BCG immunization Week 19 | M.tb. challenge Week 13 | Treatment initiation Day 0 | During treatment Week 4 | Week 8 | Week 12 | |
| Untreated | na | 2.11 (0.09) | 4.75 (0.27) | 4.71 (0.48) | 4.60 (0.27) | 4.94 (0.29) | na |
| $R_{10}$ (5/7) | | | | 3.39 (0.46) | 2.74 (0.62) | 1.27 (0.85) | na |
| $P_{15}H_{50}$ (1/7) | | | | 2.67 (0.25) | 0.79 (0.80) | 0.28 (0.41) | na |
| $B_{25}$ (5/7) | | | | 3.01 (0.45) | 0.82 (0.49) | 0.07 (0.09) | 1500 |
| $B_8$ (5/7) | | | | 3.30 (0.12) | 2.42 (0.26) | 0.69 (0.43) | 480 |
| $B_{5.33}$ (5/7) | | | | 3.83 (0.25) | 3.15 (0.47) | 1.98 (0.17) | 320 |
| $B_{2.67}$ (5/7) | | | | 3.96 (0.35) | 3.52 (0.38) | 3.16 (0.24) | 160 |
| $B_{LA-160}$ (1/28) × 3 | | | | | | 1.23 (0.16) | 480 |

TABLE 2-continued

Final *M. tuberculosis* lung CFU count data.

| | | | | Mean (SD) $\log_{10}$ *M. tuberculosis* CFU/lung at the following time points: | | | Total dose |
|---|---|---|---|---|---|---|---|
| LTBI treatment regimen* | BCG immunization Week 19 | M.tb. challenge Week 13 | Treatment initiation Day 0 | During treatment Week 4 | Week 8 | Week 12 | B over 12 weeks (mg/kg) |
| $B_{LA-160}$ (1/28) × 2 | | | | | 2.31 (0.40) | 1.63 (0.40) | 320 |
| $B_{LA-160}$ (1/28) × 1 | | | | 3.55 (0.32) | 3.31 (0.38) | 1.83 (0.34) | 160 |

*R, rifampin; P, rifapentine; H, isoniazid; B, bedaquiline, $B_{LA}$, long-acting bedaquiline formulation.
All drug doses in mg/kg indicated by subscript.
Fractions in parentheses indicate dosing frequency, in days.
SD, standard deviation.
na, not applicable.

BCG immunization. One-hundred fifty female BALB/c mice were infected by aerosol with *M. bovis* rBCG30. A culture suspension with an $OD_{600}$ of 1.03 was diluted 10-fold and then used for aerosol infection. The concentration of the bacterial suspension was 6.88 lop) CFU/mL, which resulted in a mean implantation of 3.05 (SD 0.10) $\log_{10}$ CFU/lung. Six weeks later, at the time of the *M. tuberculosis* challenge infection, the mean BCG burden in the mouse lungs was 4.95 (SD 0.11) $\log_{10}$ CFU. By Day 0, the BCG burden had decreased and stabilized at 3.27 (SD 0.45) $\log_{10}$ CFU/lung, with similar lung burdens observed in the untreated mice at Weeks 4, 8, and 12. Thus, a low-level, stable BCG infection was established in the lungs of these mice as expected.

*M. tuberculosis* challenge. Six weeks after BCG immunization, mice were infected by aerosol with *M. tuberculosis* H37Rv. A culture suspension with an $OD_{600}$ of 0.850 was diluted ~100-fold and then used for aerosol infection. The concentration of the bacterial suspension was 4.73 $\log_{10}$ CFU/mL, which resulted in a mean implantation of 2.11 (SD 0.09) lop) CFU/lung. This implantation was approximately 1 $\log_{10}$ CFU higher than was intended. By Day 0, the *M. tuberculosis* burden had stabilized at around 4.8 $\log_{10}$ CFU/lung, with similar lung burdens observed in the untreated mice at Weeks 4, 8, and 12. Thus, despite the higher implantation, a stable *M. tuberculosis* infection was established in the lungs of these mice, with the stabilized lung CFU burden correspondingly nearly 1 $\log_{10}$ CFU higher than observed in previous experiments (1-3).

Assessment of bactericidal activity (Table 2). Compared to the *M. tuberculosis* CFU counts in the lungs of untreated mice, the $R_{10}$ (5/7) control regimen reduced the mean CFU count by approximately 1, 2 and 3 $\log_{10}$ CFU/lung after 4, 8, and 12 weeks of treatment, respectively. The $P_{15}H_{50}$ (1/7) control regimen resulted in reductions of about 2, 3, and 4.5 $\log_{10}$ CFU after 4, 8, and 12 weeks of treatment, respectively. The relative magnitudes of the decline in lung CFU counts for both control regimens are as expected based on previous studies (1,2). $B_{25}$ (5/7) resulted in a reduction of about 1.7, 4.0, and 4.9 $\log_{10}$ CFU/lung after 4, 8, and 12 weeks of treatment, results which were also expected based on previous studies (1-2). Thus, the higher implantation and Day 0 CFU counts did not affect the relative activity of the drugs against this stabilized bacterial population in the mouse lungs.

For all B test regimens, there was increasing activity with increasing dose observed at Weeks 4, 8, and 12. For mice that received one or two doses of $B_{LA\text{-}160}$ (1/28), the decrease in lung CFU counts relative to untreated mice was equivalent to the decrease in mice that received the same total dose administered as a daily oral regimen, $B_8$ (5/7), for 4 or 8 weeks, respectively (p>0.05 at both time points). One dose of $B_{LA\text{-}160}$, delivering 160 mg/kg at Day 0, resulted in a decline of about 1.3 $\log_{10}$ CFU/lung, and four weeks of $B_8$ (5/7) resulted in a decline of about 1.5 $\log_{10}$ CFU/lung. After two doses of $B_{LA\text{-}160}$ (1/28) or 8 weeks of $B_8$ (5/7), the CFU counts in the lungs decreased by an additional 1 $\log_{10}$ in mice that received either of these regimens. After 12 weeks of treatment, the CFU counts in the lungs were lower in mice that had received one dose of $B_{LA\text{-}160}$ than in the mice that received the same total dose of bedaquiline (160 mg/kg) via daily dosing with $B_{2.67}$ (5/7) (p=0.0002), with the former regimen resulting in a decline of about 3 $\log_{10}$ CFU/lung and the latter resulting in a decline of 1.7 $\log_{10}$ CFU/lung, compared to the lung counts in the untreated control mice. In mice that received a total bedaquiline dose of 320 mg/kg, either through two doses of $B_{LA\text{-}160}$ or through daily dosing of $B_{5.33}$ (5/7), the decline in lung CFU counts was the same at about 3 $\log_{10}$ CFU/lung (p>0.05). For mice that received a total bedaquiline dose of 480 mg/kg via three doses of $B_{LA\text{-}160}$ (1/28), the lung CFU counts were higher than in mice that received the equivalent total dose through daily dosing with $B_8$ (5/7), although the difference was not statistically significant.

After 12 weeks of treatment, nearly all test regimens had equivalent bactericidal activity as the $R_{10}$ (5/7) control regimen, with only the $B_{2.67}$ (5/7) regimen being significantly less bactericidal than this control (p<0.0001). The test regimen $B_8$ (5/7) demonstrated equivalent bactericidal activity to both the $P_{15}H_{50}$ (1/7) and $B_{25}$ (5/7) control regimens, while all other test regimens were significantly less bactericidal than either of these control regimens at Week 12. However, CFU data recorded at the Week 12 time point may not reflect the overall efficacy of long-acting bedaquiline regimens. In mice that received a single dose of $B_{LA\text{-}160}$ on Day 0, bacterial killing was still observed 12 weeks after administration. Thus, it is conceivable that the bacterial burden in the lungs of mice that received 2 and 3 doses of $B_{LA\text{-}160}$ would still further decrease for at least 12 weeks after administration of the last dose (if not longer). Also of interest is that the single dose of $B_{LA\text{-}160}$ seemed to exert greater bactericidal activity from weeks 1 to 4 and from weeks 9 to 12, compared to weeks 5 to 8 post-administration, suggesting the possibility of biphasic B release kinetics from the long-acting vehicle.

CONCLUSIONS

Despite a higher bacterial implantation than anticipated, a stable *M. tuberculosis* infection was established in BALB/c mice that was suitable for evaluation of LTBI treatment regimens.

After 12 weeks of treatment, once-monthly dosing with $B_{LA-160}$ demonstrated superior or equivalent bactericidal activity compared to daily dosing for total bedaquiline doses of 160 or 320 and 480 mg/kg, respectively.

The bactericidal activity observed from a single dose of $B_{LA-160}$ was evident for at least 12 weeks after administration, and likely CFU counts would continue to decrease in the lungs of mice that received 2 and 3 doses. Taken together with the higher-than-expected baseline bacterial burden in this experiment, these findings suggest that cure after 2 or 3 injections may be possible. Thus, it will be critical to evaluate the sterilizing activity of these $B_{LA}$ regimens over longer time periods to truly understand their potential for use in LTBI treatment.

REFERENCES

1) Zhang, T., Li, S., Williams, K., Andries, K., Nuermberger, E. 2011. Short-course chemotherapy with TMC207 and rifapentine in a murine model of latent tuberculosis infection. Am. J Respir. Crit. Care Med. 184:732-737.
2) Lanoix, J. P., Betoudji, F., Nuermberger, E. 2014. Novel regimens identified in mice for treatment of latent tuberculosis infection in contacts of multidrug-resistant tuberculosis cases. Antimicrob. Agents Chemother. 58:2316-2321.
3) Zhang, T., M. Zhang, I. M. Rosenthal, J. H. Grosset, and E. L. Nuermberger. 2009. Short-course therapy with daily rifapentine in a murine model of latent tuberculosis infection. Am. J Respir. Crit Care Med. 180:1151-1157.

The invention claimed is:

1. A method for treating a subject infected with a pathogenic mycobacterial infection comprising administering to the subject, by intramuscular or subcutaneous injection, a composition in the form of a suspension comprising:
micro-or nanoparticles of bedaquiline, or a pharmaceutically acceptable salt thereof, and a surface modifier; and
a pharmaceutically acceptable aqueous carrier,
wherein the bedaquiline is the only active ingredient in the suspension;
wherein the amount of bedaquiline, or the pharmaceutically acceptable salt thereof, in the suspension is effective in maintaining at least a minimum plasma level of bedaquiline over a time interval of at least one month to six months.

2. The method of claim 1, wherein the pathogenic mycobacterial infection comprises *Mycobacterium tuberculosis* in a latent/dormant form or *Mycobacterium leprae*.

3. The method of claim 1, wherein the time interval is of one month to three months.

4. The method of claim 1, wherein the time interval is of three months to six months.

5. The method of claim 1, wherein the administration is preceded with a lead-in treatment phase.

6. The method of claim 5, wherein the lead-in treatment phase comprises an administration course lasting for one week, two weeks, three weeks, or one month.

7. The method of claim 1, wherein the minimum plasma level of bedaquiline is above about 10 ng/ml.

8. The method of claim 1, wherein the amount of bedaquiline, or the pharmaceutically acceptable salt thereof is calculated on a basis of about 1 mg/day to about 150 mg/day of bedaquiline.

9. The method of claim 1, wherein bedaquiline is in its non-salt or free form or in the form of a fumarate salt.

10. The method of claim 1, wherein the average effective particle size of the bedaquiline, or the pharmaceutically acceptable salt thereof, micro-or nanoparticles is below about 50 μm.

11. The method of claim 1, wherein the average effective particle size of the bedaquiline, or the pharmaceutically acceptable salt thereof, nanoparticles is below about 200 nm.

12. The method of claim 1, wherein the surface modifier is selected from the group of poloxamers, a-tocopherol polyethylene glycol succinates, polyoxyethylene sorbitan fatty acid esters, and salts for negatively charged phospholipids.

13. The method of claim 12, wherein the surface modifier is selected from Pluronic™ F108, Vitamin E TGPS, Tween™ 80, and Lipoid™ EPG.

14. The method of claim 1, wherein the relative amount (w/w) of bedaquiline to the surface modifier is in the range of 1:2 to about 20:1.

15. The method of claim 1, wherein the composition comprises by weight based on the total volume of the composition:
(a) from 10% to 70%(w/v) of bedaquiline (or a pharmaceutically acceptable salt thereof but where the w/v is calculated on the basis of its non-salt form);
(b) from 0.5% to 20%(w/v) of a wetting agent;
(c) from 0% to 10%(w/v) of one or more buffering agents;
(d) from 0% to 20%(w/v) of a isotonizing agent;
(e) from 0% to 2%(w/v) preservatives; and
(f) water for injection qs as 100%.

16. The method of claim 1, further comprising co-administering other anti-TB drugs.

17. The method of claim 1, wherein the composition is administered once.

18. The method of claim 1, wherein the composition is administered twice, wherein the administration occurs once every three months.

19. The method of claim 1, wherein the composition is administered twice, wherein the administration occurs once every three to six months.

* * * * *